United States Patent
Allbritton et al.

(10) Patent No.: US 7,157,223 B2
(45) Date of Patent: *Jan. 2, 2007

(54) METHOD AND APPARATUS FOR DETECTING ENZYMATIC ACTIVITY USING MOLECULES THAT CHANGE ELECTROPHORETIC MOBILITY

(75) Inventors: Nancy Allbritton, Irvine, CA (US); Christopher Sims, Irvine, CA (US); Michael W. Berns, Coto de Caza, CA (US); Gavin D. Meredith, Cardiff-By-The-Sea, CA (US); Tatiana B. Krasieva, Irvine, CA (US); Bruce J. Tromberg, Irvine, CA (US); Chao L. Lee, Taipei (TW)

(73) Assignee: The Regents of the University of California, Oakland, CA (US)

( * ) Notice: Subject to any disclaimer, the term of this patent is extended or adjusted under 35 U.S.C. 154(b) by 237 days.

This patent is subject to a terminal disclaimer.

(21) Appl. No.: 09/945,396

(22) Filed: Aug. 30, 2001

(65) Prior Publication Data

US 2002/0142323 A1    Oct. 3, 2002

Related U.S. Application Data

(63) Continuation of application No. 09/358,504, filed on Jul. 21, 1999, now Pat. No. 6,335,201, which is a continuation-in-part of application No. 09/036,706, filed on Mar. 6, 1998, now Pat. No. 6,156,576.

(51) Int. Cl.
    *C12Q 1/00*  (2006.01)
(52) U.S. Cl. .............. 435/4; 435/29; 435/30; 435/288.7; 435/7.4; 435/7.1; 436/2; 436/63; 436/164; 436/516; 422/82.05; 422/82.08

(58) Field of Classification Search .......... 436/63, 436/516, 164, 172, 2; 422/82.05, 82.08; 435/4, 7.1, 29, 30, 288.7, 7.4
See application file for complete search history.

(56) References Cited

U.S. PATENT DOCUMENTS

| | | | |
|---|---|---|---|
| 4,469,098 A | 9/1984 | Davi | |
| 5,071,417 A | 12/1991 | Sinofsky | |
| 5,145,567 A | 9/1992 | Hsieh et al. | |
| 5,212,382 A | 5/1993 | Sasaki et al. | |
| 5,359,615 A | 10/1994 | Sasaki et al. | |
| 5,393,957 A | 2/1995 | Misawa et al. | |
| 5,458,761 A | 10/1995 | Kamahori et al. | |
| 5,498,324 A | 3/1996 | Yeung et al. | |
| 5,505,831 A | 4/1996 | Liao et al. | |
| 5,565,171 A | 10/1996 | Dovichi et al. | |
| 5,567,292 A | 10/1996 | Madabhushi et al. | |
| 5,571,680 A * | 11/1996 | Chen ......................... | 435/7.4 |
| 5,618,284 A | 4/1997 | Zair | |
| 5,627,643 A | 5/1997 | Birnbaum et al. | |
| 5,679,536 A | 10/1997 | Hayashi et al. | |
| 5,728,687 A | 3/1998 | Bissery | |
| 6,156,576 A | 12/2000 | Allbritton et al. | |
| 6,335,201 B1 | 1/2002 | Allbritton et al. | |
| 6,740,497 B1 | 5/2004 | Allbritton et al. | |
| 2004/0161807 A1 | 8/2004 | Allbritton et al. | |

FOREIGN PATENT DOCUMENTS

| | | |
|---|---|---|
| JP | 410033197 | 2/1998 |
| WO | WO01/07910 | 2/2001 |
| WO | WO02/42732 | 5/2002 |

OTHER PUBLICATIONS

Supplementary European Search Report for application No. 0094887.5.
Supplementary European Search Report for application No. 02769700.2.
Abstract—Allbritton, N., et al., "Measurement of Kinase Activation in Single Cells", Molecular Biology Of The Cell, vol. 9, No. Suppl., Nov. 1998, p. 230 A, XP008039958 & 38th Annual Meeting of the American Society for Cell Biology; San Francisco, California, USA; Dec. 12-16, 1998; ISSN: 1059-1524.
Sims, C., et al., "Laser-Micropipet Combinattion for Single-Cell Analysis", Analytical Chemistry, American Chemical Society, Columbus, US, vol. 70, No. 21, Nov. 1, 1998, pp. 4570-4577, XP002919395, ISSN: 0003-2700.

Meredith, G., et al, "Measurement of Kinase Activation in Single Mammalian Cells", Nature Biotechnology, Nature Publishing, US, vol. 18, No. 3, Mar. 2000, pp. 309-312, XP002239303, ISSN: 1087-0156.

Lee, C., et al., "Localized Measurement of Kinase Activation in Oocytes of Xenopus Laevis", Nature Biotechnology, Nature Publishing, US, vol. 17, No. 8, Aug. 1999, pp. 759-762, XP002185167, ISSN: 1087-0156.

Maru, Y., "Molecular Biology of Chronic Myeloid Leukemia", International Journal of Hematology, vol. 73, No. 3, Apr. 2001, pp. 308-322, XP008040048, ISSN: 0925-5710.

Baruch, A., et al., "Enzyme Activity—It's All About Image", Trends in Cell Biology, vol. 14, No. 1, Jan. 2004. pp. 29-35, XP002309365, ISSN: 0962-8924.

Adams et al., "The Analysis of Multiple Phosphoseryl-Containing Casein Peptides Using Capillary Zone Electrophoresis," J. Chromatography, 1993, pp. 391-396, vol. 646.

Bao et al., "Determination of Minute Enzymatic Activities by Means of Capillary Electrophoretic Techniques," J. Chromatography, 1997, pp. 481-497, vol. 699.

Cann et al., "A Tyrosine Kinase Assay Using Reverse-Phase High-Performance Liquid Chromatography," Anal. Biochem., 1997, pp. 327-333, vol. 247.

Chen et al., "Chemical Analysis of Single Cells and Exocytosis," Crit. Rev. Neurobiol., 1997, pp. 59-90, vol. 11.

Chiu et al., " Probing Single Secretory Vesicles with Capillary Electrophoresis," Science, 1998, pp. 1190-1193, vol. 279.

Craig et al., "Monitoring Protein Kinase and Phosphatase Reactions with Matrix-Assisted Laser Desorption/Ionization Mass Spectrometry and Capillary Zone Electrophoresis: Comparison of the Detection Efficiency of Peptide-Phosphopeptide Mixtures," Biol.I Mass Spectrometry, 1994, pp. 519-528, vol. 23.

Cruz et al., "Nitrite and Nitrate Levels in Individuals Molluscan Neurons: Single-Cell Capillary Electrophoresis Analysis," J. Neurochem., 1997, pp. 110-115, vol. 69.

Dawson et al., "A Capillary Electrophoresis-Based Assay for Protein Kinases and Protein Phosphatases Using Peptide Substrates," Anal. Biochem., 1994, pp. 340-345, vol. 220.

Erim et al., "Performance of a Physically Adsorbed High-Molecular-Mass Polyethyleneine Layer as Coating for the Separation of Basic Proteins and Peptides by Capillary Electrophoresis," J. Chromatography, 1995, pp. 356-361, vol. 708.

Ewing, "Microcolumn Separation of Single Nerve Cell Components," J. Neurosci. Meth., 1993, pp. 215-224, vol. 48.

Floyd et al., "Capillary Electrophoresis Analysis of Nitride Oxide Synthase Related Metabolites in Single Identified Neurons," Anal. Chem., 1998, pp. 2243-2247, vol. 70.

Fuller et al., "Single Neuron Analysis by Capillary Electrophoresis with Fluorescence Spectroscopy," Neuron, 1998, pp. 173-181, vol. 20.

Gilman et al., "Analysis of Single Cells by Capillary Electrophoresis with On-Column Derivatization and Laser-Induced Fluorescence Detection," Anal. Chem., 1995, pp. 58-64, vol. 67.

Giuliano et al., "Fluorescent Protein Biosensors: Measurement of Molecular Dynamics in Living Cells," Annu. Rev. Biophys. Struct., 1995, pp. 405-434, vol. 24.

Hepala, "Breaking the Barrier: Methods for Reversible Permeabilization of Cellular Membranes," Critical Reviews in Biotechnology, 1997, pp. 105-122, vol. 17.

Hernandez et al., "Laser-Induced Fluorescence and Fluorescence Microscopy for Capillary Electrophoresis Zone Detection," Chromatography, 1991, pp. 183-196, vol. 23.

Higashi et al., "Imaging of cAMP-Dependent Kinase Activity in Living Neural Cells Using a Novel Fluorescent Substrate," FEBS Lett., 1997, pp. 55-60, vol. 414.

Hoffmann, "The Potential for Isoenzyme-Selective Modulation of Protein Kinase C," Faseb J., 1997, pp. 649-669, vol. 11.

Hogan et al., "Determination of Intracellular Species at the Level of a Single Erythrocyte Via Capillary Electrophoresis with Direct and Indirect Fluorescence Detection," Anal. Chem., 1992, pp. 2841-2845, vol. 64.

Isbell et al., "A Non-Radioactive Fluorescent Method for Measuring Protein Kinase C Activity," Life Sciences, 1995, pp. 1701-1707, vol. 57.

Jankowski et al., "Assaying Single Cells with Capillary Electrophoresis," Trends in Anal. Chem., 1995, pp. 170-176, vol. 14.

Kennelly et al., "Consensus Sequences as Substrate Specificity Determinants for Protein Kinases and Protein Phosphatases," J. Biol. Chem., 1991, pp. 15555-15558, vol. 226.

Klann et al., " Mechanism of Protein Kinase C Activation During the Induction and Maintenance of Long-Term Potentiation Probed Using a Selective Peptide Substrate," Proc. Natl. Acad. Sci. USA, 1993, pp. 8337-8341, vol. 90.

Lee et al., "Quantitative Determination of Native Proteins in Individual Human Erythrocytes Capillary Zone Electrophoresis with Laser-Induced Fluorescence Detection," Anal. Chem., 1992, pp. 3045-3051, vol. 64.

Lillard et al., "Separation of Hemoglobin Variants in Single Human Erythrocytes by Capillary Electrophoresis with Laser-Induced Native Fluorescence Detection," J. Chromatography, 1995, pp. 397-404, vol. 718.

Lillard et al., "Monitoring Exocytosis and Release from Individual Mast Cells by Capillary Electrophoresis with Laser-Induced Native Fluorescence Detection," Anal. Chem., 1996, pp. 2897-2904, vol. 68.

Lillard et al., "Capillary Electrophoresis for the Analysis of Single Cells: Laser-Induced Fluorescence Detection," Handbook of Capillary Electrophoresis, J.P. Landers, Boca Raton, FL, CRC Press, pp. 523-544.

Luzzi et al., "Localized Sampling of Cytoplasm for Xenopus Oocytes," Anal. Chem., 1997, pp. 4761-4767, vol. 23.

Mcilroy et al., "A Continuous Fluorescence Assay for Protein Kinase C," Anal. Biochem., 1991, pp. 148-152, vol. 195.

Miller et al., "Enzymatic Profiling of Immobilized Cells Using CZE," Anal. Chem., 1994, pp. 24240-2423, vol. 66.

Pihel et al., "Electrochemical Detection of Histamine and 5-Hydrozytryptamine at Isolated Mast Cells," Anal. Chem., 1995, pp. 4514-4521, vol. 67.

Post et al., "A Fluorescent Protein Biosensor of Myosin II Regulatory Light Chain Phosphorylation Reports a Gradient of Phosphorylated Myosin II in Migrating Cells," Mol. Biol. Cell, 1995, pp. 1755-1768, vol. 6.

Regnier et al., "Electrophoretically-Mediated Microanalysis (EMMA)," Trends in Anal. Chem., 1995, pp. 177-181, vol. 14.

Sala-Newby et al., "Engineering Firefly Luciferase as an Indicator of Cyclic AMP-Dependent Protein Kinase in Living Cells," FEBS Lett., 1992, pp. 241-244, vol. 307.

Snow et al., Anal. Biochem., 1999, pp. 36-42, vol. 271.

Tan et al., "Simultaneous Determination of Enzyme Activity and Enzyme Quantity in Single Human Erythrocytes," Anal. Biochem., 1995, pp. 74-79, vol. 226.

Tsien, "The Green Fluorescent Protein," Annu. Rev. Biochem., 1998, pp. 509-544, vol. 67.

Wu et al., Anal. Biochem., 1999, pp. 423-425, vol. 269.

Xue et al., "Determination of Lactate Dehydrogenase Isoenzymes in Single Lymphocytes from Normal and Leukemia Cells Lines," J. Chromatography, 1996, pp. 233-240, vol. 677.

Xue et al., Anal Chem., 1994, pp. 1175-1178, vol. 66.

Yeung, "Chemical Analysis of Single Human Erythrocytes," Acc. Chem. Res., 1994, pp. 409-414, vol. 27.

Zhang et al., Electrophoresis, 1996, pp. 372-378, vol. 17.

Zhao et al., Glycobiology, 1994, pp. 239-242, vol. 4.

Abstract - Kirkpatrick, et al., Energy Res. Abstracts vol. 4, No. 15, Abstr. No. 41711, 1979.

Abstract - Theis, et al., Clinical Cardiology, vol. 6, No. 8, pp. 396-398, 1983.

Abstract - Solgonick, et al., Journal of Endourology, vol. 7, No. 5, pp. 371-373, Oct. 1993.

Abstract - Krasieva, et al., Proc. SPIE - Int. Soc. Opt. Eng., vol. 3260, pp. 38-44, 1998.

Yang, Q., et al., "Trends in Capillary Electrophoresis: 1997", Journal of Chromatographic Science, vol. 35, pp. 358-373, (1997).

Capillary Zone Electrophoresis with Electrochemical Detection in 12.7 um Diameter Columns, Anal. Chem. 1988, 60, Wallingford, et al., pp. 1972-1975.
Capillary Electrophoresis in 2 and 5 um Diameter Capillaries: Application to Cytoplasmic Analysis, Anal. Chem, 1990, 62, Olefirowicz et al., pp. 1872-1876.
Microcolumn Separations and the Analysis of Single Cells, Kennedy et al., Science, vol. 246, pp. 57-63, (1989).
Monitoring single-cell pharmacokinetics by capillary electrophoresis, etc. Journal of Chromatography B, 689, 1997, Tong et al., pp. 321-325.
Discovery of endogenous catecholamines in lymphocytes and evidence for catecholamine regulation of lymphocyte function via an autocrine loop., Proc. Natl. Acad. Sci., USA, Bergquist, J., et al., vol. 91, pp. 12912-12916, (1994).
Kinetic Perfection in Enzymatic Catalysis: The $k_{cat}/K_M$ Criterion., Biochemistry textbook by Stryer, p. 195, Mar. 1, 1995.
Inositol Trisphosphate and calcium signaling, Nature, vol. 361, 1993 Berridge, pp. 315-325.
A review of In Vitro Studies: Low-Frequency Electromagnetic Fields, American Industrial Hygiene Assoc. J., vol. 54, Cleary, 1993, pp. 178-185.
A critical review of the genotoxic potential of electric and magnetic fields, Mutation Research, 1993, McCann et al., vol. 297, pp. 61-95.
Formation and resealing of pores of controlled sizes in human erythrocyte membrane, Nature vol. 268, 1977, Kinosita, JR et al., pp. 438-441.
Electroporation-Induced Formation of Individual Calcium Entry Sites in the cell body and processes of adherent cells., Biophysical Journal, vol. 73, 1997, Teruel et al., pp. 1785-1796.
Manipulation of a single cell with microcapillary tubing based on its electrophoretic mobility, Electrophoresis 1995, Kitagawa et al., vol. 16, pp. 1364-1368.
Focal Adhesions, Contractility, and Signaling, Annual Reviews Cell Dev. Biology, 1996, Burridge et al.,vol. 12, pp. 463-519.
Regulation of extracellular matrix synthesis by mechanical stress, Biochem. Cell Biol. 74, 1996, Chiquet et al., pp. 737-744.
Tensegrity: The Architectural Basis of Cellular Mechanotransduction, Annual Reviews Physiol., 1997, Ingber, vol. 59, pp. 575-599.
Mechanisms of Intraocular Photodisruption with Picosecond and Nanosecond Laser Pulses, Lasers in Surgery and Medicine 1994, Vogel et al., vol. 15, pp. 32-43.
The Interaction of a single laser-generated cavity in water with a solid surface, 1996, J. Acoustical Society of America, Shaw et al., vol. 99, No. 5, pp. 2811-2824.
Shock wave emission and cavitation bubble generation by picosecond and nanosecond optical breakdown in water, 1996, J. Acoustical Society of Am., Vogel, et al., vol. 100, No. 1, pp. 148-165.
Alteration of cell membrane by stress wave in Vitro, Ultrasound in Med . & Biol., vol. 22, No. 9, 1996, Lee et al., pp. 1285-1293.
Stress-Wave-Induced Injury to Retinal Pigment Epithelium Cells In Vitro, Lasers in Surgery and Medicine, 1996, Douki, et al., vol. 19, pp. 249-259.
Transcellular transport of fluorescein in hepatocyte mono-layers: Evidence for functional polarity of cells in culture, Proc. Natl. Acad. Sci. USA, vol. 79, Aug. 1982, Barth, et al., pp. 4985-4987.

* cited by examiner

*Primary Examiner*—Long V. Le
*Assistant Examiner*—Deborah A. Davis
(74) *Attorney, Agent, or Firm*—Evan Law Group LLC

(57) ABSTRACT

The activity of intracellular chemical reactions of molecules is measured by the use of fluorescently labeled substrate molecules that undergo a change in electrophoretic mobility upon chemical reaction such as that catalyzed by an enzyme. Specificity is achieved by using labeled substrate molecules that can be acted upon only by specific enzymes. Thus the activity of a specific enzyme or class of enzymes can be determined. Measurements are made with the intracellular presence of such substrate molecules, at some time of interest, typically after exposure of the cell to a stimulus that activates a particular enzymatic pathway. To ensure accuracy, measurements must be made in a timely manner so as to minimize chemical reactions occurring subsequent to the time of interest. Fast controllable laser lysis is used to obtain the contents of a single cell into which reporter substrate molecules have been introduced. The cell contents are then subjected to capillary electrophoresis and enzymatic activity is determined by comparing amounts of substrate molecules to amounts of enzymatically altered substrate molecules which are separated by the electrophoresis and identified by the presence of a fluorescent label.

25 Claims, 12 Drawing Sheets

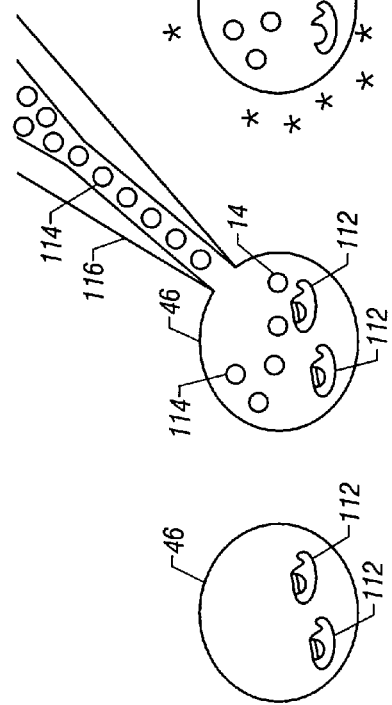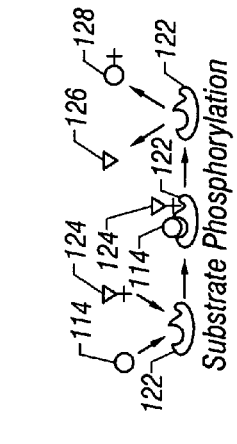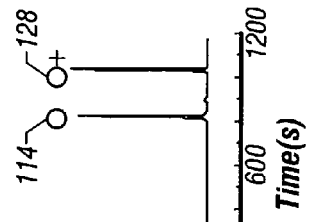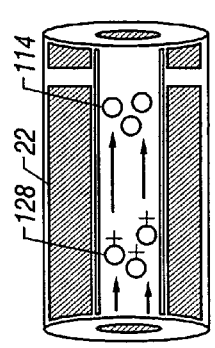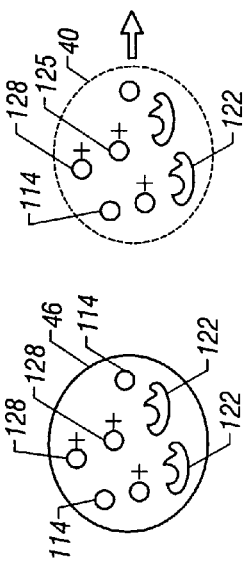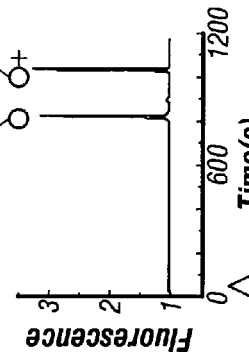

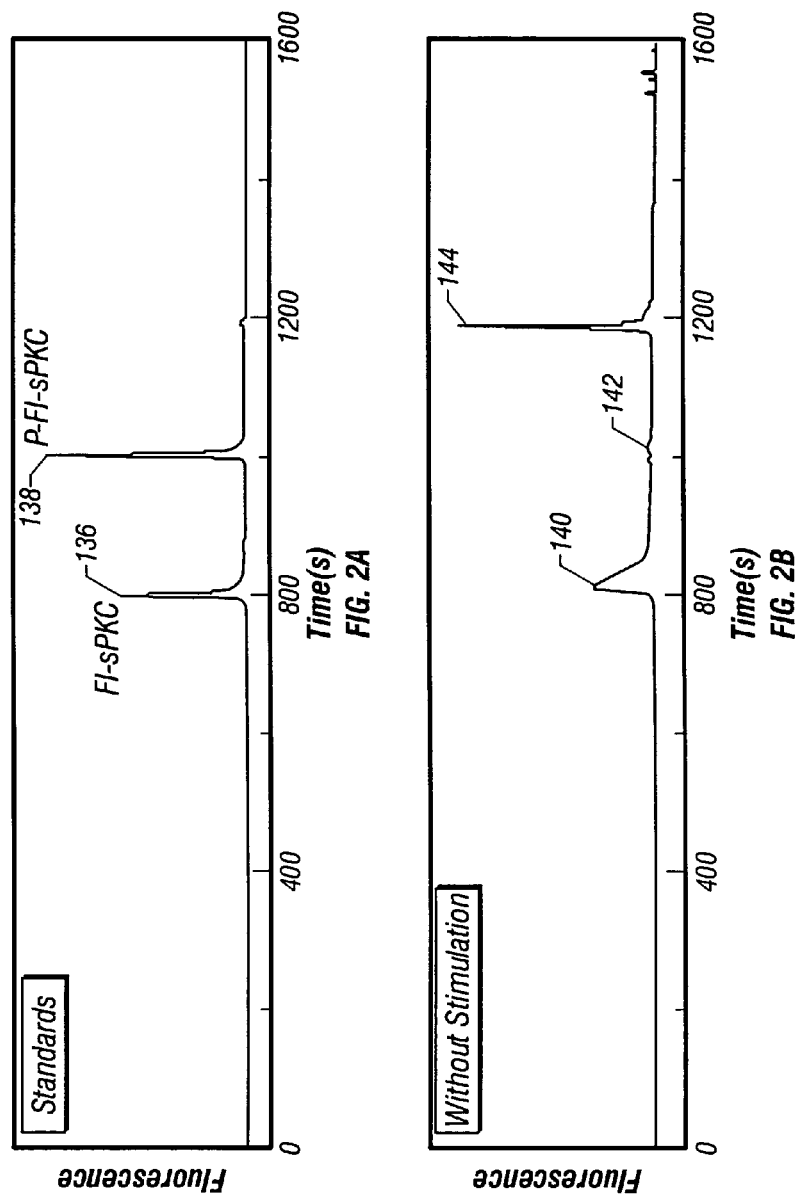

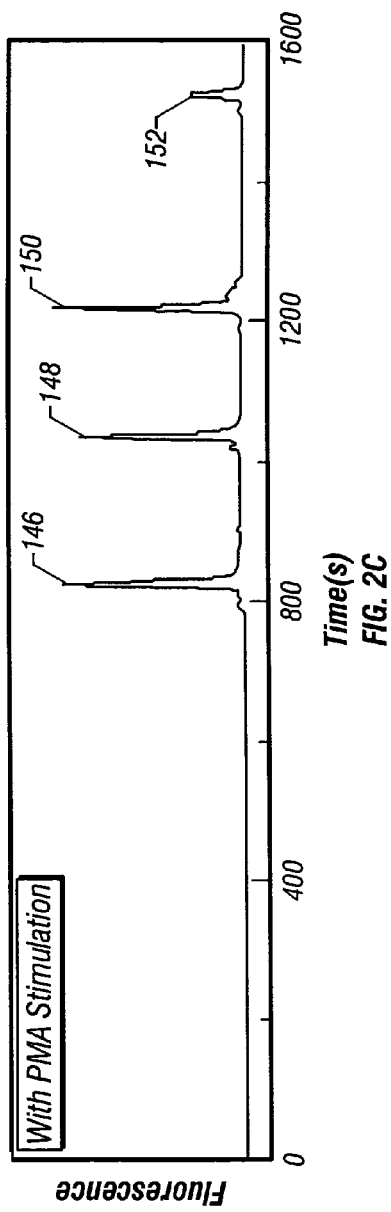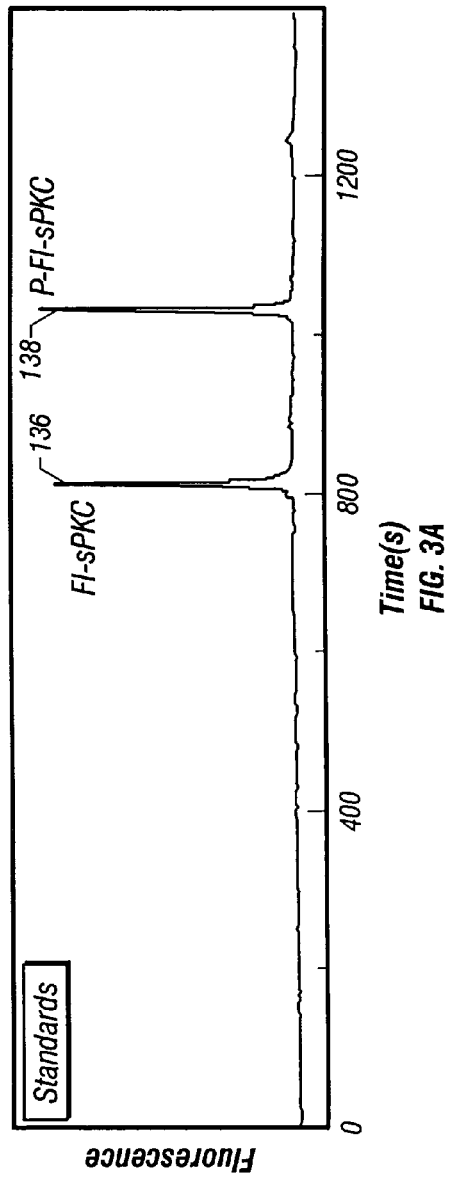

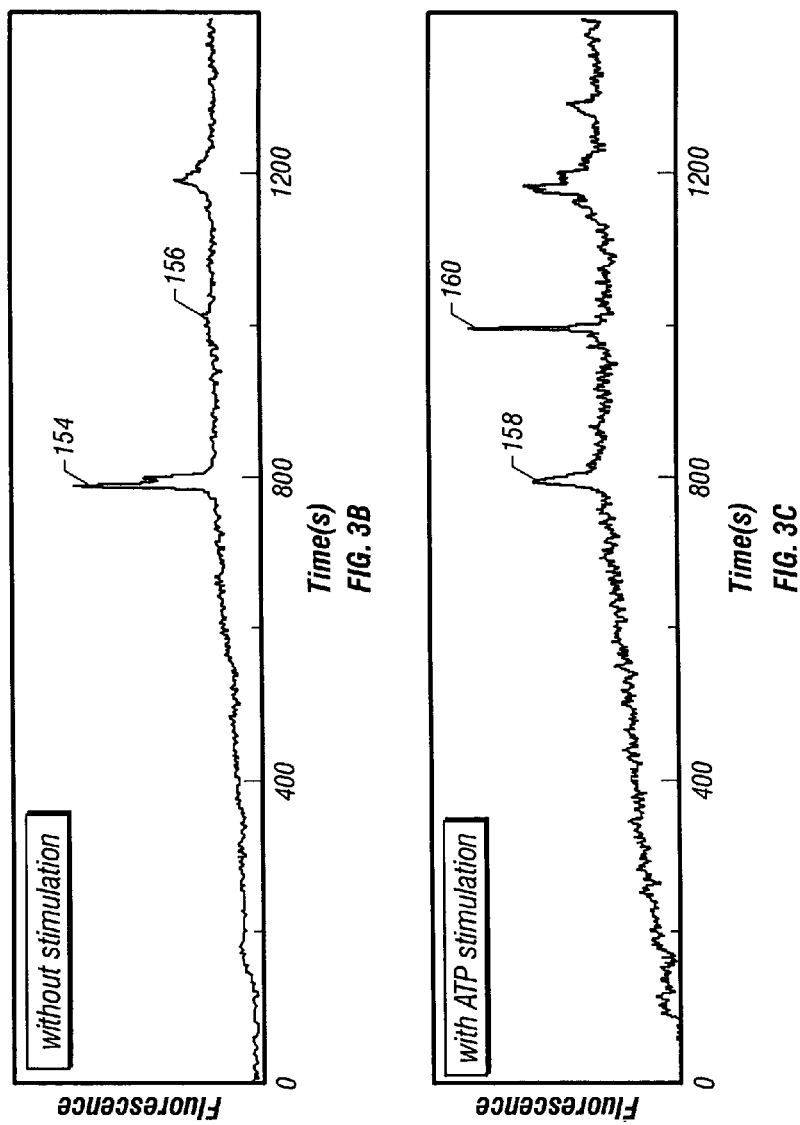

METHOD AND APPARATUS FOR DETECTING ENZYMATIC ACTIVITY USING MOLECULES THAT CHANGE ELECTROPHORETIC MOBILITY

RELATED APPLICATIONS

The present application is a continuation of application Ser. No. 09/358,504, now U.S. Pat. No. 6,335,201 (2002) filed on Jul. 21, 1999, which in turn was a continuation-in-part application of application Ser. No. 09/036,706, now U.S. Pat. No. 6,156,576 (2000), filed Mar. 6, 1998, entitled "Fast Controllable Laser Lysis of Cells for Analysis".

BACKGROUND OF INVENTION

1. Field of the Invention

The invention relates to the field of micro-analytical chemistry in the areas of cellular biochemical and biomedical analysis, and in particular to a class of chemical compounds and method and apparatus for assaying the internal chemical activity of a single cell or selected cells.

2. Description of the Prior Art

In biology, the individual cell can be thought of as the fundamental unit of life. Ultimately, the chemical processes that occur within single cells give rise to all of the phenomena that we observe in living organisms. Most intracellular chemical processes are mediated by proteins. Typically these proteins are enzymes that catalytically enhance the rates of specific chemical reactions. Very often, intracellular enzymes participate in cascades of chemical reactions known as signal transduction pathways. Each of these signal transduction pathways is composed of sequentially acting enzymes, frequently of a class known as kinases. These enzymes not only interact with and modify the behavior of other proteins within the same pathway, but also influence the operation of other signal transduction pathways. These interacting cascades of signaling molecules and chemical reaction products form complex networks that ultimately regulate processes of cell growth, proliferation, quiescence, and programmed cell death.

Inappropriate signaling within a cell can give rise to defects in any of these processes and is implicated as the basis for many forms of cancer. To further complicate matters, individual cells display a high degree of heterogeneity in their internal biochemical signaling. Malignant tumors are typically composed of such a heterogeneous group of cells, and cells within the same tumor often utilize disparate and aberrant growth signaling pathways. This heterogeneity makes it necessary to analyze individual cells to elucidate their unique errors in signaling. Where only a small proportion of cells show aberrant signaling, analysis of an entire population will produce an average signal more reflective of the majority rather than of any individual aberrant cell. Thus, the measurement "averages out" the very errors one seeks to detect.

Often there is a genetic basis, in the form of mutations in genes for signaling proteins, for inappropriate signaling. Mutations in the genes for signaling proteins result in the presence of structurally altered, aberrantly acting, signaling proteins. Currently, there exist methods to analyze the DNA and/or RNA of a single cell to detect the presence of signaling protein mutations and thereby infer the presence of mutant signaling proteins. However, it is not currently possible to predict or understand errors in signaling purely from knowledge of the genes or mutations in the genes that occur within a tumor. For example, the aberrant activity of mutant signaling proteins in one pathway may be counteracted or modified by the activities of other proteins, mutant or normal, involved in other pathways. This is very likely since the interior of a tumor cell is a complex mixture of signaling proteins generally with hundreds to thousands of different kinds present simultaneously and participating in pathways that frequently influence one another. To assess the function of any single kind of a signaling protein, its net activity must be measured from within a single living cell.

Further, to completely describe the function of an entire pathway, measurements of the activities of all the signaling proteins involved within a pathway are needed. Such knowledge would be exceptionally useful in the individualized diagnosis and treatment of diseases that involve faulty intracellular signaling since signaling proteins are often prime targets for therapeutic drug intervention.

Further, such a capability would revolutionize the ability to conduct research on basic cellular physiology. As noted, kinases represent an exemplary class of protein enzymes that commonly play a key role in intracellular signaling. In fact, aberrant activation of growth promoting kinases is a general feature of tumor cells. Thus protein kinases are promising targets for cancer therapies and the development of kinase antagonist drugs is an area of intense research. These enzymes catalytically enhance the rate at which a covalent chemical bond is formed between a phosphate group and a molecular substrate molecule, frequently, a different protein. This process is termed "phosphorylation". When the substrate itself is an enzyme, such phosphorylation generally either enhances or suppresses the substrate enzyme's chemical activity.

Kinases generally demonstrate substrate specificity such that the preferred substrates of one kind of kinase are not efficiently phosphorylated by other kinds of kinases. Frequently, the preferred substrates for kinases are different kinases; thus, the inappropriate activity of one kinase can result in changes in the activity of multiple downstream kinases within a signaling pathway.

A general method to measure kinase activity within a cell could, in many instances, yield an abundance of information about an entire signaling pathway. However, in order to make such a measurement strict criteria must be met. To begin with, the number of copies per cell of many enzymatic proteins, such as kinases and kinase substrates, can be as low as 100 to 1,000,000 molecules, or about 150 pM to 1.5 μM in concentration in a typical mammalian cell with a volume of 1 pl. In terms of moles, this is equivalent to a necessary limit range of approximately $1.7 \times 10^{-18}$ to $1.7 \times 10^{-22}$.

Further, since the concentrations of phosphorylated substrantes in cells change on time scales of the order of seconds, the time resolution of the measurement, from the instant the contents of the cell are obtained to the time that the biochemical reactions are terminated, must be subsecond. Most conventional biochemical assays meet neither the temporal resolution nor the sensitivity limits required for these single cell measurements. The temporal, resolution requirement can be met through the use of apparatus described in U.S. Pat. No. 6,156,576 (2000), filed Mar. 6, 1998, and entitled, "Fast Controlla6l1e Laser Lysis of Cells for Analysis", to which this continuation-in-part application is related and which parent application is herein expressly incorporated by reference. The necessary degree of sensitivity can be achieved with traditional capillary electrophoresis (CE) methods. Lacking, until now, has been the molecular means to accurately determine the intracellular activity of one or more kinase species or other enzymes.

Current techniques for kinase measurements can generally be divided into three methodologies. The first method uses the phosphorylation of kinase substrates by cellular extracts to estimate the kinase activity that occurs within intact cells. There are a number of major drawbacks to such a method. Because it is not sensitive, the internal contents of large numbers of cells must be pooled. Since the cells are not synchronous with respect to their activation status, a time averaged level of kinase activity is actually measured. Furthermore, during the time required to generate a cellular extract, a time that may span many seconds to minutes, many chemical reactions continue to proceed. This results in a highly distorted representation of the relative amounts of reactants and products as they occurred within actual cells.

Even beyond these difficulties, it is virtually impossible to reproduce the unique chemical microenvironments that occur within cells; thus, the chemical activity observed in extracts can differ greatly from that which actually occurs within intact cells.

A second methodology relies on labeling the kinase within a cell with specific antibodies, kinase inhibitors, or fluorescent tags and then observing the cells with a fluorescence microscope. Both inactive and active kinase molecules are labeled by this method, and an attempt is then made to infer the activity level of the kinase from its actual location within a cell. However, it is extremely risky to attempt to determine the state of activation of an enzyme solely from its intracellular location. This is particularly true for a number of kinases that are active both when free in the cell and also when bound to intracellular structures.

A third method, still under development, is the use of a fluorescent indicator to actually measure kinase activity. A similar strategy has worked well for the measurement of various intracellular ion concentrations (i.e. $Ca^{2+}$), but thus far has not been generally applicable to the measurement of kinase activities. One of the drawbacks of this approach is the need for a supraphysiologic concentration of a reporter fluorophore to produce sufficient signal for ready detection-typically 10 µM to 100 µM of fluorescent indicators are necessary within cells for detection by fluorescence microscopy. This is 10 to 1,000,000 times the concentration of typical physiological kinase substrates. At such high concentrations the fluorescent reporter molecule may behave as an inhibitor or may induce other unintended cellular responses such as activation of aberrant signaling pathways. Another difficulty has been that the viscous, highly concentrated, intracellular environment alters the fluorescent properties of the reporter molecule making the detection unreliable.

Finally, the design of fluorescent, environment-sensitive probes for a specific kinase may not be generally applicable to other kinases. Because a given cell or group of cells may contain a large number of different kinases, this may pose a serious problem. The need for broadly applicable, accurate, and sensitive cellular measurement technologies is great.

What is needed is an alternative, yet complementary, strategy to the above approaches. Further, this new approach should be one that it is not limited to the measurement of kinases, but is broadly adaptable to the measurement of many if not all other kinds of intracellular enzymatic and chemical activities.

BRIEF SUMMARY OF INVENTION

The present invention is a method for measuring intracellular chemical activity. Typically the molecules of interest are intracellular enzymes, proteins that catalyze biochemical reactions within cells. Catalysis by enzymes results in the alteration of the chemical structure of substrate molecules. The invention comprises the use of substrate molecules that undergo a change in electrophoretic mobility when enzymatically acted upon as intracellular reporters of chemical activity. This strategy provides a general method to detect and quantify enzymatic activity by measuring changes in the structure of substrate molecules. A change in electrophoretic mobility allows for separation of enzymatically altered substrate molecules from unaltered substrate molecules by electrophoresis with highly sensitive detection and quantification methods following separation. Even very minor changes in chemical structure can result in measurable differences in electrophoretic mobility. For example, capillary electrophoresis is routinely used to separate stereoisomeric forms of chemical compounds.

Most commonly, substrate molecules are selected to report on the activity of a specific enzyme or class of enzymes. These reporter substrate molecules can occur naturally within a cell, be induced within a cell, such as when under the control of an operon or similar genetic control mechanism, or be introduced into a cell by a variety of established methods including, but not limited to, microinjection, electroporation, optoporation, vesicle fusion, pinocytic loading, or by association with membrane permeant peptides. The reporter substrate molecules may be naturally occurring compounds or synthetically derived. Measurements are made with the intracellular presence of such substrate molecules, at some time of interest, typically after exposure of a cell to a stimulus. At the time of interest, part or all of the contents of a single cell or group of cells are harvested for separation by capillary electrophoresis. To ensure accuracy of measurement, this process must be achieved in a timely manner so as to minimize chemical reactions occurring subsequent to the time of interest. In practice, this means that if a measurement is to be made to within an accuracy of 1%, then less time should pass, from the time of interest to the time of termination of chemical reactions, than is required for the progress of a reaction to change by 1%. Typically, chemical reactions are terminated by physical disruption as with detergents, turbulent mixing, dilution, or separation of molecules by electrophoresis, or by a combination of these processes. Fast controllable laser lysis is an excellent way to harvest, on a sub-second time scale, the contents of a single cell into which reporter substrate molecules have been introduced.

Reporter molecules specific for particular intracellular reactions can be designed to undergo a predictable change in electrophoretic mobility. These molecules can also be modified to be fluorescent and thus detectable in the minute amounts and low concentrations that occur within the tiny volumes of single cells. In the illustrated embodiments, modified peptides are used as representative reporter molecules. Modified peptides are a particularly useful class of such possible reporter molecules for a number of reasons. Foremost, peptides closely mimic natural, endogenous protein substrates and frequently demonstrate a high degree of specificity in the reactions in which they participate and thus report. This can be understood to be the result, in many cases, of the unique primary sequence structure of these peptides. The particular order of amino acid residues that comprises a given peptide conveys unique chemical properties to the molecule, particularly with regards to being recognized and acted upon as a substrate by a particular enzyme. Typically, enzymes whose natural substrates are proteins will efficiently catalyze only those reactions involving molecules that display a particular order or pattern of amino acid residues.

Peptides are extremely versatile compounds when used as reporter substrates. Large, diverse libraries of these compounds can be generated simply by varying the sequence and number of amino acid residues that comprise a given peptide. Furthermore, modifications of basic peptide structure can be made in a number of ways. For example, D-isomer amino acids can be incorporated into peptides in place of the more commonly found L-isomeric forms. Also, unusual or alternate, non-naturally occurring amino acids can be incorporated into peptides. Examples include homo-arginine and homo-lysine in place of arginine and lysine, respectively. Even the backbone peptide bond may be altered. After modifications such as these have been made, the resultant peptides have proven to serve as substrates for enzymatic reactions.

In the illustrated embodiments, the modified peptides are substrates for enzymes known as kinases that alter the peptides by the addition of a phosphate moiety to a specific amino acid(s) within the peptide. Phosphorylation can be effected in vitro, in the absence of a cell, and leads to a demonstrable alteration of the peptides' chemical structure and electrophoretic mobility.

Further, the peptides used in the illustrated embodiments are modified at at least one point, frequently the end by covalent addition of a fluorescein group (or other fluorescent group) to allow detection by laser-induced fluorescence. The fluorescent tags can be added to either the amino or carboxyl termini or to specific amino acid residues by chemical techniques well-known to those of skill in the art. Examples of readily modifiable residues include the sulfhydryl group of cysteine, the amino groups of arginine and lysine, and the carboxyl groups of aspartate and glutamate. Example chemical groups that react with sulfhydryl groups include maleimides, iodoacetamides, alkyl halides, aziridines, and epoxides. Chemical groups that react with amines include succinimydyl esters, sulfonyl halides, isothiocyanates, and aldehydes. Chemical groups that react with carboxyls include carbodiimides, hydrazines, alkyl halides, amines, and diazoalkanes. A wealth of different fluorophores, with reactive groups, are commercially available for covalent linkage to peptides at these groups. Examples of different fluorophores that are available include fluorescein derivatives such as Oregon Green produced by Molecular Probes (Eugene, Oreg.), rhodamine derivatives such as Texas Red and tetramethylrhodamine, NBD (7-nitrobenz-2-oxa-1,3,diazole) derivatives, coumarins, dansyl derivatives, pyrenes, and the cyanine dyes (Cy-3/Cy-5) produced by Amersham/Pharmacia Biotech (Piscataway, N.J.). This diversity allows the preparation of peptides that absorb and emit light at wavelengths ranging from the ultraviolet through the visible and into the infrared parts of the spectrum. This is yet another avenue that can be exploited to produce a large variety of reporter substrate peptides with differing spectral properties.

While illustrative, the invention is not contemplated to be limited to use of modified peptides alone or in its scope to the monitoring of reactions by intracellular kinases alone. It is contemplated that a broader range of intracellular chemical reactions can be monitored by this approach. For example, peptide-based reporter substrates may be designed to report on the activities of phosphatases, glycosylases, acetylases, proteases and caspases, and isomerases. It is also contemplated that molecular reporters may be based on other chemical species commonly found in cells such as nucleic acids, carbohydrates, phospholipids, and entire proteins or may be based on compounds (often polymers) not ordinarily found within cells. Nucleic-acid based reporter molecules could serve as excellent substrates for nucleases, ligases, polymerases, methylases, demethylases, and nucleotide transferases. Lipid based reporter substrates could serve to monitor lipases. Carbohydrate based reporters could serve to monitor oxidoreductases, glycosylases, hydrolases, lyases, and isomerases. Finally since entire proteins are frequently the natural substrates for intracellular chemical reactions, reporters based on these could prove to yield extremely accurate information about intracellular physiology.

Reporter molecules that comprise entire proteins may be based on the green fluorescent protein (GFP) from the jellyfish *Aequorea victoria*. This protein is intrinsically fluorescent and has been used extensively in basic biological research. The gene for the protein has been cloned and mutated to produce a diversity of GFP-like fluorescent proteins that have unique absorption and emission spectra. A gene for a GFP-like protein can be linked to genetic sequences for either a peptide or an entire protein. Upon expression within a cell, such a chimeric molecule has the fluorescent properties of GFP along with the properties of the linked peptide or protein. When the linked peptide or protein is a substrate, the result is a protein-based fluorescent molecular substrate. Such a chimeric molecule can be produced in bacteria or cultured eukaryotic cells and purified for use as an exogenous reporter substrate, or the gene can be introduced into the cell of interest for the endogenous production of reporter substrate. In fact, such a gene can be introduced into a cell-line to produce a new cell-line that carries the gene from one generation to the next. After intracellular turnover and sub-cellular sampling, electrophoresis can be used to separate the GFP-linked turned-over substrate molecules from non-turned over GFP-linked substrate molecules. It is clear that genes for fluorescent proteins exist in other organisms, such as *Renilla*, that are not identical to the GFP from *Aequorea*, and it is expected that when these genes are cloned they will be similarly utilized.

Detection of molecular reporter molecules, obtained from within a cell, need not be achieved only by fluorescent methods. Fluorescent methods are generally utilized because of the extremely low limits of detection that they provide. In fact, fluorescence-based methods have been developed that can allow the detection of single molecules. As illustrated in Table 1, the necessary detection limit to observe the amount of substrate found in a 1 pl (picoliter) mammalian cell at a physiologically normal concentration of 1 µM, is $10^{-18}$ mol or about 600,000 molecules. Alternative quantitative optical spectroscopic detection methods based on phosphorescence or chemiluminescence can also achieve this low limit of detection. Also some electroanalytical methods such as amperometry or voltammetry are sensitive enough to be used to detect and quantify altered and unaltered reporter molecules obtained from single cells. Sensitive detection and quantitation has also been achieved by coupling electron ion-spray mass spectrometry to capillary electrophoretic separation. Incorporation of heavy atoms into the reporter molecules, either from elements rare to biological systems or in the form of unusual isotopes, could greatly increase the utility of such mass spectrometry.

TABLE 1

| | MAMMALIAN CELL (RBL) | XENOPUS OOCYTE | CONVENTIONAL IN VITRO ASSAY* |
|---|---|---|---|
| Volume Assayed | 1 pl ($10^{-12}$ liters) | 22 pl ($2.2 \times 10^{-11}$ liters) | 37.5 μl ($3.75 \times 10^{-5}$ liters) |
| Concentration of Substrate | 1 μM ($10^{-6}$ mol/l) | 1 μM ($10^{-6}$ mol/l) | 10 μM ($10^{-5}$ mol/l) |
| Total Amount Measured | $10^{-18}$ mol (~600,000 molecules) | $2.2 \times 10^{-17}$ mol (~13,300,000 molecules) | $3.75 \times 10^{-10}$ mol (~226,000,000,000,000 molecules) |

*Promega (Madison, WI) PKC Assay-normal instructions followed

Multiple reporter substrates, each reporting on a specific chemical reaction, are expected to be utilizable simultaneously within a given cell.

Finally, it is anticipated that the use of reporter molecules, as disclosed herein, will have utility in contexts that are not exclusively intracellular. This approach will be generally applicable to the measurement of chemical activities in circumstances where minute volumes, low concentrations, and miniscule quantities occur. An example of a non-cellular volume that could be assayed with such reporter molecules is the interior of a liposome or vesicle, a single-cell sized, or smaller, compartment that is typically enclosed by lipid molecules.

The invention and its various embodiments, now having been summarized, may be better understood by viewing the following drawings wherein like elements are referenced by like numerals.

BRIEF DESCRIPTION OF THE DRAWINGS

FIGS. 1A–H are schematic illustrations, in stages, showing the measurement of an intracellular kinase according to the invention. A legend is included with FIG. 1A to identify the molecular species depicted.

FIG. 1A is a diagrammatic depiction of a cell in a possible state prior to measurement wherein the cell contains inactive kinase molecules.

FIG. 1B a diagrammatic depiction of the cell of FIG. 1A after introduction of reporter substrate molecules.

FIG. 1C is a diagrammatic depiction of the cell of FIG. 1B during extracellular treatment with a stimulant that leads to activation of the intracellular kinase.

FIG. 1D is a schematic representation of the reporter substrate phosphorylation as catalyzed by an active kinase molecule.

FIG. 1E is a diagrammatic depiction of the cell of FIG. 1C after some degree of reporter substrate has been phosphorylated.

FIG. 1F is the cell of FIG. 1E after disruption of its plasma membrane to obtain the contents for analysis in FIG. 1G.

FIG. 1G represents the separation of nonphosphorylated and phosphorylated substrate molecules by capillary electrophoresis (CE).

FIG. 1H shows a typical electrophoretogram in which a population of nonphosphorylated reporter substrate molecules has been separated from a population of phosphorylated reporter substrate molecules.

FIGS. 2A–C is the graph of three stacked electrophoretograms of reporter substrate molecule separations all made under identical electrophoretic conditions on the same day.

FIG. 2A is the graph of an electrophoretogram showing the separation of nonphosphorylated and in vitro phosphorylated reporter substrate molecules from a mixture in buffer solution, to be viewed as a reference for the electrophoretic mobilities of both species.

FIG. 2B is the graph of an electrophoretogram of the contents of a rat basophilic leukemia (RBL) cell, a tumor cell, that was microinjected and in which protein kinase C Stat (PKC) was not specifically activated (FIG. 3B shows a similar treatment).

FIG. 2C is the graph of an electrophoretogram showing the separation from the contents of an RBL cell in which protein kinase C (PKC) was specifically activated.

FIGS. 3A–C is the graph of three stacked electrophoretograms of reporter substrate molecule separations all made under identical electrophoretic conditions on the same day.

FIG. 3A is the graph of an electrophoretogram showing the separation of nonphosphorylated and in vitro phosphorylated reporter substrate molecules from a mixture in buffer solution to establish a standard for the electrophoretic mobilities of both species.

FIG. 3B is the graph of an electrophoretogram showing the separation from the contents of a rat basophilic leukemia cell in which PKC was not specifically activated.

FIG. 3C is the graph of an electrophoretogram showing the separation from the contents of an RBL cell in which PKC was activated.

FIG. 4A is the graph of an electrophoretogram that shows the mobility of the nonphosphorylated form of the reporter substrate in buffer.

FIG. 4B is the graph of an electrophoretogram that shows the mobility of the phosphorylated form of the reporter substrate in buffer.

FIG. 4C is the graph of an electrophoretogram that shows the separation of a sample of the contents of a Xenopus oocyte that had been previously microinjected to contain a reporter substrate.

FIG. 4D is the graph of an electrophoretogram that shows the separation of a sample of the contents of a Xenopus oocyte that had been previously microinjected to contain a reporter substrate which has been specifically activated.

FIG. 8A is a diagram of a device for holding and sampling an oocyte (or similar cell) and rapidly subjecting the sample to electrophoresis.

FIG. 8B is a diagram of a microscope, capillary, and fluorescence detection setup employing the device of FIG. 8A.

FIG. 11A is the graph of an electrophoretogram showing separation of nonphosphorylated and in vitro phosphorylated reporter substrate molecules from a mixture in buffer solution as a reference for the electrophoretic mobilities of all species of reporter molecules.

FIG. 11B is the graph of an electrophoretogram of the contents of an RBL cell in which PKC was not specifically activated.

FIG. 11C is the graph of an electrophoretogram of the contents of an RBL cell in which PKC was activated.

Figure 4A:
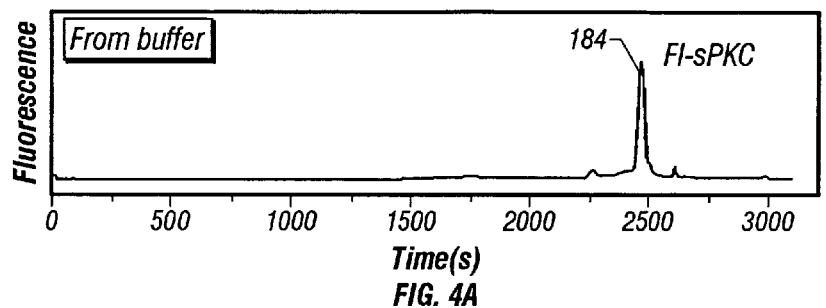
FIGS. 4A–D is the graph of four stacked electrophoretograms of reporter substrate molecule separations all made under identical electrophoretic conditions on the same day. (The electrophoretic conditions differ from those used in FIGS. 2A–C and 3A–C.)

The invention and its various embodiments may now be understood by turning to the following Detailed Description of the Preferred Embodiments.

DETAILED DESCRIPTION OF THE PREFERRED EMBODIMENTS

In the illustrated embodiment the contents of the cell or cellular component thereof is collected within one second or less of lysis of the cell. This is of utility when the cell is living so that the biological reactants can be analyzed in the state which they had obtained at the instant of lysis. In fact the contents are collected within 33 msec or less of lysis of the cell and it is believed that collection is delayed only by the time for the cell or cellular component to porate or open, which is believed to be a few microseconds or in the range of 1–10 microseconds of lysis of the cell.

The collection after lysis and the lysis itself is fast. The collector delivers at least a portion of the contents of the lysed cell or cellular component to the analysis device within one second of lysis of the cell or cellular component. Where applied to a living cell the contents of the lysed cell or cellular component is delivered to the analysis device within 33 msec of lysis of the cell or cellular component and in all probability within 1–10 microseconds of lysis of the cell or cellular component.

By positioning the inlet of a capillary directly above the cell prior to lysis, the cellular contents of the lysed cell are loaded into the lumen of the capillary by combination of the gravity siphon and electrophoresis at lysis. The force of the shock wave also conveys momentum to the cell fragments which drive them into the lumen of the capillary. As will be shown below the time required between the instant of the beginning of lysis and the loading within the lumen is significantly less than 33 msec.

The step of collecting at least a portion of the contents of the cell or cellular component thereof may further comprise the step of stopping the reactions of biochemical reactants disrupted from the selected cell or cellular component thereof to permit subsequent analysis of the biochemical reactants in the state which existed approximately at the time of disruption.

Where the cell or cellular component is free floating the step of controllably positioning the selected cell or cellular component in the medium in another embodiment comprises the step of temporarily holding the cell or cellular component in a position in the medium by a laser microbeam optical tweezers, or temporarily holding the cell or cellular component in a position in the medium by adhesion of a mechanical micromanipulator to the cell or cellular component.

In the illustrated embodiment the step of collecting at least a portion of the contents of the disrupted cell or cellular component thereof in the analysis device is by means of fluid flow of the medium, and in particular by means of siphon fluid flow of the medium. Collection can also be effected by means of electrophoresis through the medium, by means of force from the shock wave impacted on the contents, and by means of electroosmotic force. The use of a capillary with charged lumenal walls allows the use of electroosmotic flow, and loading the cell's contents by the gravity siphon flow could be eliminated, if desired. The use of any type of mechanism beyond siphon, electrophoretic, electroosmotic and shock wave forces to collect the cell contents into a pipette is expressly included in the scope of the invention.

The substrate is collected by means of a microlumen in the capillary or microfabricated channel of a micropipette.

In the first illustrated embodiment the net activity of an intracellular enzyme known as protein kinase C (PKC) is measured by first introducing into a single mammalian cell of ~1 pl volume, by means of microinjection, a synthetic fluorescent peptide that is a substrate for phosphorylation by PKC. Upon phosphorylation by PKC, the net charge of the fluorescent peptide substrate is altered from +5 to +3. More significantly, the charge-to-mass ratio of the peptide substrate changes as a result of this chemical alteration.

Consequently, when the contents of the single cell are obtained by means of fast, controllable laser lysis, separated by capillary electrophoresis, and detected by laser-induced fluorescence, one or two identifiable populations of molecules are observed and quantifiable. The populations are identified by reference to the characteristic migration time observed for each molecular species when individually subjected to capillary electrophoresis. The faster migrating population of molecules, observed as a peak of induced fluorescence by a photomultiplier tube, corresponds to substrate that is not phosphorylated. The slower population, also observed as a peak of induced fluorescence, corresponds to substrate that has been phosphorylated. This difference in migration rate through a capillary 22 is referred to as a change in electrophoretic mobility. The difference in electrophoretic mobility between the two populations of molecules is a consequence of the difference in the charge-to-mass ratio of the molecules in each population and the particular conditions used to carry out electrophoresis.

In this case, PKC phosphorylation of a subset of substrate molecules has altered their characteristic electrophoretic mobility. The relative amounts of the molecules within the two populations give a measure of the net PKC activity that occurred within the single cell up to the time of lysis. Where the cell is not treated to activate its PKC, most of the detectable substrate peptide is in the nonphosphorylated form. When the cell is exposed to chemicals that are activators of PKC for five minutes, approximately half the measured substrate peptide is of the phosphorylated form. These measurements have been taken from individual cells of two unrelated mammalian cell lines, rat basophilic leukemia (RBL) cells, a cultured granulocyte cell line, and NIH/3T3 cells, a mouse (murine) fibroblast cell line. Further in this embodiment, it is demonstrated that two different fluorescent peptides that are reporters for the activity of two distinct kinases can be simultaneously detected and identified from the contents of a single RBL cell.

In another embodiment, the net activity of PKC within a single frog (Xenopus) oocyte 46', an approximately 1 mm in diameter, 1 µl in volume, nonmammalian cell, is measured. In this case, the same synthetic fluorescent peptide substrate is introduced by injection into the cell. Subsequently, a portion of the contents of the cell are removed with a sharpened capillary tip that is guided by a piezoelectric motor. In this case, the contents of the oocyte 46' need not be harvested by laser lysis because the oocyte 46' is large enough to be mechanically sampled. Once a portion of the contents are in the capillary 22, they are separated under electrophoretic conditions that have been empirically optimized for the separation of oocyte cytosolic components. Although differing cells and electrophoretic conditions are used as compared to the first embodiment, identifiable and quantifiable populations of phosphorylated and nonphosphorylated PKC substrate molecules are still obtained. Additional measurements from the oocytes 46' at multiple time points allowed the average rate of stimulated substrate phosphorylation to be determined for treatment of the oocytes 46' with two different chemical activators of PKC.

Finally in this embodiment, it is demonstrated that three different fluorescent substrate peptides that are reporters for the activity of three different distinct kinases can be detected and identified from a portion of the contents of a single frog oocyte 46'.

Shared Aspects of Two Illustrated Embodiments

Two preferred embodiments are presented. The first pertains to the measurement of intracellular chemical activity in single small mammalian cells that are typically 5–10 µm in diameter and about 1 pl in volume. This is illustrated by measurements made from individual rat basophilic leukemia (RBL) cells of the cell line RBL-2H3 and from individual murine NIH/3T3 cells. The second pertains to the measurement of intracellular chemical activity in relatively large single cells. In this second embodiment, measurements are made from individual Xenopus laevis frog oocytes 46' that are about 1 mm in diameter and about 1 µl in volume. In both illustrated embodiments, measurements of the activity of intracellular protein kinase C (PKC) are made from individual cells. In both embodiments, the same reporter substrate molecule is used, termed Fl-sPKC for "fluorescent substrate of PKC". Upon phosphorylation by PKC, the net charge of the Fl-sPKC is altered from +5 to +3. More significantly, the charge-to-mass ratio changes as a result of this chemical alteration. Subsequently, when the contents of the single cell are obtained, separated by capillary electrophoresis, and detected by laser-induced fluorescence, one or two identifiable populations of molecules, corresponding to nonphosphorylated and/or phosphorylated Fl-sPKC, are observed and quantifiable. A comparison of the quantities involved (volume assayed, concentration of substrate, and total amount) in these PKC measurements and in a conventional radiographic method is provided in Table 1.

The sequence of amino acid residues that comprises this reporter peptide is derived from a region of the PKC protein sequence. The peptide sequence, as found in the larger PKC sequence, Arg-Phe-Ala-Arg-Lys-Gly-<u>Ala</u>-Leu-Arg-Gln-Lys-Asn-Val, is known to inhibit the enzyme, but when the underlined alanine residue is substituted with a serine residue, the resulting sequence is known to serve as a relatively specific substrate for PKC. Thus, the sequence of Fl-sPKC is Fl-Arg-Phe-Ala-Arg-Lys-Gly-<u>Ser</u>-Leu-Arg-Gln-Lys-Asn-Val, where "Fl" stands for a fluorescein moiety that was covalently attached to the amino terminal end of the peptide following standard peptide synthesis. The underlined serine residue, <u>Ser</u>, is the phosphorylation site. Resin-bound, nonfluorescent sPKC peptide was obtained from the Stanford PAN facility and generated by conventional synthetic methods. The peptide with fluorescein covalently bound to the amino terminus was prepared by incubating 5-carboxyfluorescein succinimidyl ester (100–200 mg/ml, Molecular Probes, Eugene, Oreg.) with resin-bound nonfluorescent peptide (30 mg/ml peptide), 1-hydroxybenzotriazole (57 mg/ml), and N,N diisopropylethylamine (55 mg/ml) in dimethylformamide for 12 hours on a rotating mixer. The peptide was washed with dimethylformamide and ethyl acetate, and then cleaved from the resin by incubation for two hours with a trifluoroacetic acid (TFA)/free-radical scavenger mix (trifluoroacetic acid (84%, v/v), phenol (0.2%, wt/v), thioanisol (5%, v/v), ethanediol (2.5%, v/v), water (8.5%, v/v)), previously sparged with argon or nitrogen. The peptide was separated from the resin by passage through a sintered glass filter. The peptide was then precipitated by addition of ice cold ether, dissolved in acetic acid (5%), and subsequently lyophilized. The peptide was purified by reverse phase high pressure liquid chromatography (HPLC) on a semipreparative C18 column (Alltech, Deerfield, Ill.) with a gradient of 0.1% trifluoroacetic acid in water and 0.1% trifluoroacetic acid in acetonitrile. The concentration of the fluorescein-labeled peptide, Fl-sPKC dissolved in buffer A (135 mM NaCl, 5 mM KCl, 10 mM HEPES, 2 mM $MgCl_2$, and 2 mM $CaCl_2$ adjusted to pH 7.4 with NaOH), was determined by comparing its fluorescence to that of standards of hydrolyzed carboxyfluorescein succinimidyl ester. Fl-sPKC purity was assessed by reverse phase high pressure liquid chromatography on an analytic C18 column (Alltech) and by capillary electrophoresis. The peptide was stored in 2 µl aliquots at $-70°$ C.

In both embodiments, reference separations, as illustrated in FIGS. 2A, 3A, 4A and 4B, of the reporter substrate peptide, Fl-sPKC, and its phosphorylated form, referred to as P-Fl-sPKC, were performed in buffer. Generation of P-Fl-sPKC for this purpose was achieved by in vitro phosphorylation. Fl-sPKC (4–40 µM) was phosphorylated by rat brain PKC (1.2 µg/ml, Molecular Probes, Eugene, Oreg.) in the presence of dioctanoylglycerol (25 µg/ml, Avanti Polar Lipids, Alabaster, Ala.), phosphatidylserine (250 µg/ml), $MgCl_2$ (10 mM), Tris HCl (50 mM, pH 7.5), adenosine triphosphate (1 mM), and $Ca^{2+}$ (~10 µM). The free $Ca^{2+}$ concentration was set by addition of 10 mM EGTA with 10 mM calcium. The reaction mixture was incubated at room temperature for one hour and the phosphorylated peptide was used without further purification.

The general scheme of the measurements in both embodiments is depicted in FIGS. 1A–H. FIGS. 1A–H are schematic illustrations, in stages, showing the measurement of an intracellular kinase according to the invention. A legend is included with FIG. 1A to identify the molecular species depicted. FIG. 1A is a diagrammatic depiction of a cell 46 in a possible state prior to measurement wherein the cell contains inactive kinase molecules 112.

A Measurement

The course of a measurement begins with introduction of Fl-sPKC into the cell of interest, such as depicted in FIG. 1B. In this case, microinjection of a reporter substrate 114 through a micropipet 116 is depicted.

In measurements where the cell 46 is treated with a stimulant 118 to activate intracellular PKC, the stimulant 118 is added into a solution 120 surrounding the cell 46 as depicted in FIG. 1C.

FIG. 1D is a schematic representation of the reporter substrate phosphorylation as catalyzed by an active kinase molecule. Adenosine triphosphate (ATP) 124, normally within the cell 46 at all times, is the intracellular source of phosphate groups for this reaction. The active kinase 122 catalyzes the reaction of the nonphosphorylated reporter substrate 144 with ATP 124. After phosphorylation, adenosine diphosphate (ADP) 126 is released along with the phosphorylated reporter substrate 128.

Phosphorylation of Fl-sPKC, as generally diagrammed in FIG. 1D, occurs to the greatest extent in cells that are treated with the stimulant 118, resulting in cells 46 with internal contents as depicted in FIG. 1E. FIG. 1E is a diagrammatic depiction of the cell 46 of FIG. 1C after some amount of the reporter substrate has been phosphorylated. After a given time interval, in cases both with stimulant treatment and without, all or a portion of the intracellular contents of the cell 46 are loaded into a capillary 30 for separation and detection. FIG. 1F is a diagrammatic depiction of the cell 46 of FIG. 1E after disruption of its plasma membrane, shown in dotted outline, to liberate the cellular contents for analysis and for separation in the capillary 22 in FIG. 1G. FIG. 1G diagrammatically depicts the separation of nonphosphorylated and phosphorylated substrate molecules 114 and 128, respectively, by capillary electrophoresis (CE) symbolically shown by the distance of separation between nonphosphorylated and phosphorylated substrate molecules 114 and 128, respectively, within the capillary 30.

An optical window 38 at the distal end of the capillary 30 allows interrogation by a laser (not shown) and collection of laser-induced fluorescence as represented in the combination FIGS. 1F–G by flow of material from the cell 46 with a disrupted plasma membrane into the capillary 30.

In both embodiments a photomultiplier tube (PMT) is used to collect argon laser (488 nm) induced fluorescence for detecting the presence and amount of Fl-sPKC and P-Fl-s PKC. Although the light collection systems used differ slightly, in both embodiments the photomultiplier tube current was amplified and converted to a voltage with a preamplifier, and this signal was digitized by a data acquisition board in a personal computer. The output is diagrammatically depicted in FIG. 1H, which shows a typical electrophoretogram in which a population of the nonphosphorylated reporter substrate molecules 114 has been separated from a population of the phosphorylated reporter substrate molecules 128.

Figure 9:
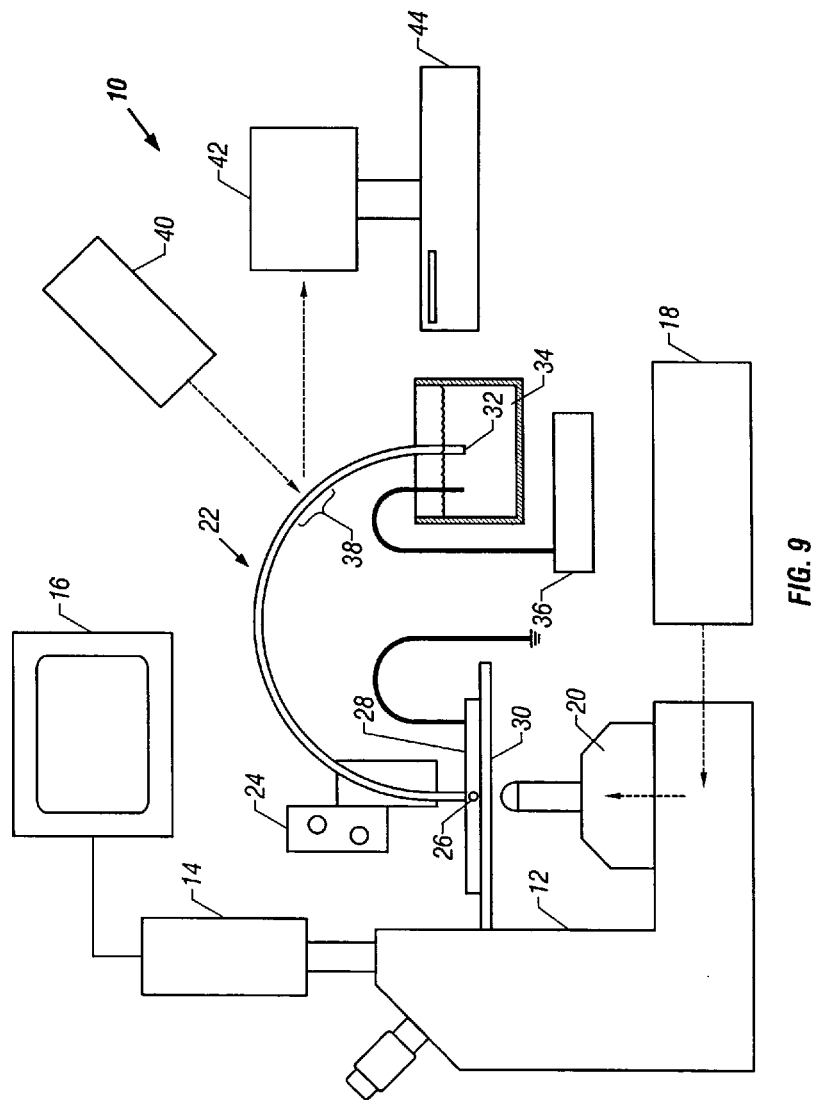
FIG. 9 is a diagrammatic depiction of the fast lysis apparatus used in the illustrated embodiment.

FIG. 9 is a diagrammatic depiction of the fast lysis apparatus used in the illustrated embodiment in which fast controlled cell lysis is performed in combination with analysis by capillary electrophoresis. The system is described in the incorporated parent application, but the basic description is set forth again for convenience. It must be understood that many components now known or later devised may be substituted into the system of FIG. 1A to perform equivalent functions. For example, although the illustrated embodiment contemplates laser induced fluorescence detection of analytes in an electrophoretic column, any measurement device or detection mechanism capable of analyte detection or analysis may be used with any separation system capable of separating reporter molecules on the basis of charge, or charge-to-mass ratio.

The system, generally denoted by reference numeral 10, is comprised of a microscope 12 having a video ocular readout 14 displayed on a CRT screen 16 or recorded by a videotape recorder or digital recorder (not shown). In particular, as will be described below, digital storage of the images and pattern processing in a computer system for automated cell processing and analysis is specifically contemplated as being within the scope of the present invention. A CCD (charge coupled device) video camera system 14, 16 recorded the real time bright field image of the cell 46 every 33 milliseconds. Lysis was determined from the appearance of the cell after the laser pulse. In most cases, the cell membrane was totally disrupted, leaving behind only a remnant of the membrane attached to a cover slip 36 with the cellular contents suspended in the immediate vicinity of the (former) cell. In the illustrated embodiment, electrophoresis was initiated by a voltage pulse sent by the laser at the time of operator-triggered firing and consequent lysis. It is to be expressly understood that computer-controlled pattern recognition could be substituted for operator viewing and firing could likewise be autonomously triggered.

A pulsed Nd:YAG laser 18 is directed through a microscope objective 20 of a microscope 12. The laser system used for the cell lysing experiment included a frequency doubled Q-switched Nd:YAG laser such as manufactured as the Surelite I, so by Continuum of Santa Clara, Calif. The laser was used to generate a single laser pulse of 1 to 25 µJ with a 5 nsec pulse with a 532 nm wave length. The laser beam from the laser 18 was directed into the microscope 12, an Axiovert 135 manufactured by Zeiss of Thornwood, N.Y. The laser pulse was focused to approximately 0.3 to 0.4 µm at its waist 50 as shown in FIG. 1B using the microscope objective 20 (100×, 1.3 n.a. Zeiss) at the interface of the cell chamber cover slip 36 and buffer solution 54. The cell 46 which was to be lysed was positioned 10–20 µm laterally to the focal point 50 of the laser pulse. Lysis, disruption of the cell's outer membrane, is effected by a shock wave that is generated by the laser pulse. It is to be expressly understood, however, that in another embodiment direct interaction may be arranged, such as where the laser parameters are adjusted only to open a hole in the cell membrane to expel the cytoplasmic contents, leaving the nuclear material within. It must be understood that other types of lasers other than the one illustrated here may also be used to generate the shock wave. In addition to lysis of the cell, the nucleus of the cell which has been isolated or removed from the cell may by manipulated to recover the DNA or other nuclear material.

A fused silica capillary column 22 is positioned by means of a micromanipulator 24 which positions a proximate inlet 26 of the capillary 22 above a cover slip or slide 28 positioned on the microscope stage 30. The buffer solution around the cell and above the cover slip is electrically grounded. A high voltage power supply, model CZE 1000R manufactured by Spellman of Plainview, N.Y., was used to drive the electrophoresis in the column or capillary 22. The fused silica capillary 22 had a 50 µm inner diameter and 360 µm outer diameter. The total length of the capillary 22 was 90 to 100 cm. A detection window 38 was about 75 cm from the inlet end 26. Electrophoresis was performed in a biologically compatible buffer. The cell chamber 199 of FIG. 10 served as an inlet reservoir and was held at ground potential. The outlet reservoir was held at 10 to 18 kV. The inlet end 26 of the capillary 22 was used as a micropipette for introducing the cellular contents into the capillary 22 after cell lysis.

After removing 5 mm of polyimide coating from the capillary 22 above the inlet end 26, the inlet end 26 was mounted perpendicularly to the cover slip 36 on a micromanipulator 24. The micromanipulator 24 enabled precise positioning of the capillary lumen 52 with respect to the cell 46 to be lysed and loaded into the capillary 22. The capillary 22 was washed after every run. Gravitational siphon fluid flow was used to load the capillary 22 with phosphorylated/nonphosphorylated peptide standards. The loaded volumes were calculated from Poiseulle's equation.

The capillary 22 includes the optical detection window 38 upon which an excitation beam from the Argon laser 40 is aimed. Fluorescence data were collected at a right angle to the capillary 22 and to the laser beam from the laser 40 by a 40× microscope objective with a 0.75 n.a., Plan Fluor manufactured by Nikon of Melville, N.Y. The collected light was measured by a photomultiplier tube, a PMT R928 made by Hamamatsu, of Bridgewater, N.J., after spectral filtering through a 488 nm notch filter, manufactured by Kaiser Optical Systems of Ann Arbor, Mich., and a band pass filter 535 DF55, made by Omega Optical of Brattleboro, Vt. The photomultiplier current was amplified and converted to a voltage with a preamplifier then digitized by a data acquisition board in a personal computer 44. The data were plotted and peak areas calculated using Origin written by Microcal of North Hampton, Mass. Induced fluorescence data are used to create the electrophoretograms of FIGS. 2A–C, 3A–C, 4A–D, 5, 7, and 11. The bath 34 is electrically coupled to a high voltage source 36 to provide the electrophoretic force to cause analyte separation in the capillary 22.

Conditions and Results Unique to the First Embodiment

The Cells Used

FIGS. 2A–C and 3A–C are two sets of graphs of three stacked electrophoretograms of reporter substrate molecule separations all made under identical electrophoretic conditions on the same day. In the first embodiment, illustrated by FIGS. 2A–C and FIGS. 3A–C, rat basophilic leukemia (RBL) cells, from the tumor mast cell line RBL-2H3, were used. These cells were grown at 37° C. and 5% $CO_2$ in Dulbecco's modified eagle medium (DMEM) supplemented with 10% fetal bovine serum, and L-glutamine (584 g/l). Penicillin (100 units/ml) and streptomycin (100 µg/ml) were added to the media to inhibit bacterial growth. The cells 46 were grown in a chamber 199 made by using Sylgard (Dow Corning, Midland, Mich.) to attach a silicon "O" ring (15/16 in. outer diameter—not shown) to a 25 mm, round, no. 1, glass cover slip (not shown). Cell attachment to the glass surface was enhanced by coating the cover slip with Cell-Tak (Becton Dickinson, Bedford, Mass.) prior to adding the cells 46 to the cell chamber 199. Prior to use, the cells 46 were allowed to grow in supplemented media for 12–24 hr after plating in the cell chamber 199. The cells 46 were plated at concentrations determined empirically to produce approximately one cell per 100× field of view on the day of the measurement. Tissue culture materials were obtained from Gibco BRL (Gaithersburg, Md.). Murine NIH/3T3 cells, as used in FIG. 12, were grown under identical conditions except that the use of Cell-Tak was omitted and the cells were typically allowed to grow 24–48 hours after plating in the cell chamber 199. Murine NIH/3T3 cells grow to approximately the same dimensions as do RBL cells.

Microscopy and Cell Sampling

In the first embodiment, the microscopy system of FIG. 9 used for cell lysis was similar to that described previously in the incorporated application entitled "Fast Controllable Laser Lysis of Cells for Analysis". The frequency-doubled Q-switched Nd:YAG laser 18 (Minilite II, Continuum, Santa Clara, Calif.; Minilase II-20, New Wave Research, Sunnyvale, Calif.) was used to generate a single pulse (1–25 µJ, 5-ns pulse width, 532 nm) directed into a fluorescence microscope 12 (Axiovert 135, Zeiss, Thornwood, N.Y.). The pulse was focused (~0.3–0.4 µm at its waist) with a microscope objective 20 (100×, 1.3 n.a., Fluor, Zeiss) within the cover slip 36 adjacent to its interface with the buffer. This same microscope objective 20 was used for visual observation during cell microinjection and selection. The cell 46 to be lysed was positioned 10 µm lateral to the focal point of the laser pulse so that no direct interaction of the laser beam with the cell 46 occurred. Lysis was effected by manual triggering of a Nd:YAG laser pulse. In most cases, the cell membrane was completely disrupted leaving behind only a remnant of the cell membrane attached to the cover slip.

Separation Conditions

In the first embodiment, electrophoresis was performed in a 50–75 cm long, fused-silica, uncoated capillary 22 (360 µm outer diameter, 50 µm internal diameter) from Polymicro Technologies (Phoenix, Ariz.) using buffer A, a physiologically compatible extracellular buffer composed of 135 mM NaCl, 5 mM KCl, 10 mM HEPES, 2 mM $MgCl_2$, and 2 mM $CaCl_2$ and adjusted to pH 7.4 with NaOH. The cell chamber 199 served as the inlet reservoir and was held at ground potential. An outlet reservoir was held at a negative voltage of 10.8–13.4 kV with a high-voltage power supply (CZE1OOOR, Spellman, Plainview, N.Y.). The electrophoretic current was 50–70 µA. The inlet 26 of the capillary 22 was used as a micropipet for introducing the cellular contents into the capillary 22 following cell lysis. Electrophoresis was initiated simultaneously with lysis by electrically triggering the voltage difference off the laser pulse. The inlet and outlet ends 26 and 32 respectively of the capillary 22 were held at the same height during cell lysis, loading and electrophoresis to eliminate flow due to gravity. Between electrophoretic runs, the capillary 22 was washed by the following regimen:
  1) buffer A was manually forced though the capillary 22 with a handheld syringe for 30 sec (approximately 10 column volumes);
  2) doubly distilled, reverse-osmosis treated water (Milli-Q) was forced through for 30 seconds;
  3) 1 N NaOH was forced through for 5 min.;
  4) Milli-Q water was forced through for 30 sec.;
  5) 0.1 N HCl was forced through for 3 min.;
  6) Milli-Q water was forced though for 30 sec.; and
  7) buffer A was forced though for 1 min.

Detection

For the purpose of detection, a 5 mm length of the polyimide coating was removed from the outer surface of the capillary 22 at a position 12.5 cm from the outlet end 32 to create a window 38. The coating was removed by brief heating with a disposable butane lighter and was subsequently cleaned with a 70% ethanol solution. The capillary 22 lumen was interrogated through the optical window 38 by the focused beam of an argon ion laser (488 nm, Uniphase, San Jose, Calif.). The laser beam was focused by a lens (not shown) with a focal length of 3.8 cm (CVI, Albuquerque, N.Mex.). Fluorescence data were collected by a detector 42 at a right angle to the capillary 22 and the laser beam with a microscope objective (not shown, but included in the detector 42—40×, 0.75 n.a., Plan Fluor, Nikon, Melville, N.Y.), and the light measured with a photomultiplier tube (not shown, but included in the detector 42—PMT, R928, Hammamatsu, Bridgewater, N.J.) after spectral filtering with a 488 nm notch filter (Kaiser Optical Systems, Ann Arbor, Mich.) (not shown, but included in the detector 42) and a 535DF55 band-pass filter (Omega Optical, Brattleboro, Vt.) (not shown, but included in the detector 42). The photomultiplier tube current was amplified and converted to a voltage with a model 1212 preamplifier (DL Instruments, Dryden, N.Y.) (not shown, but included in the detector 42). The signal was digitized by a data acquisition board (DAS-1800, Keithly Metrabyte, Taunton, Mass.) in a personal computer 44 (Gateway, Sioux City, S.Dak.).

The data were plotted and peak areas calculated using Origin (Microcal, Northhampton, Mass.). The system could easily detect ~6×10$^{-21}$ mol (about 3600 molecules) of Fl-s PKC, well below the limit of detection required for physiologically relevant measurement (see Table 1).

Electrophoretic Migration Standards

FIGS. 2A and 3A are two graphs of an electrophoretogram showing the separation of nonphosphorylated and in vitro phosphorylated reporter substrate molecules from a mixture in buffer solution, to be viewed as a reference for the electrophoretic mobilities of both species. To obtain the electrophoretic migration standards as shown in FIGS. 2A and 3A, dilute mixtures of Fl-sPKC and P-Fl-sPKC were loaded into the capillary 22 by gravitational fluid flow and the loaded volume calculated from Poiseulle's equation. These mixtures were approximately 1 nM in concentration of both species in FIG. 2A and approximately 100 pM in concentration of both species in FIG. 3A. FIGS. 2A and 3A each show a nonphosphorylated Fl-sPKC peak 136 and a phosphorylated P-Fl-sPKC peak 138 for the standards.

Figure 11A:
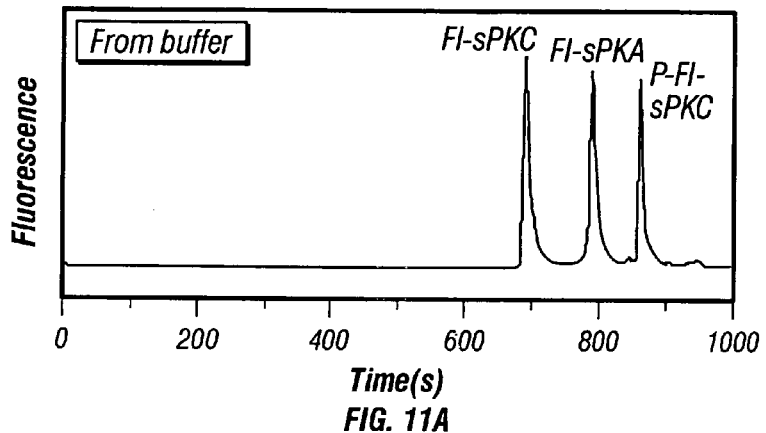
FIGS. 11A–C is the graph of three stacked electrophoretograms of reporter substrate molecule separations all made under identical electrophoretic conditions on the same day.

FIG. 11A is also a graph of an electrophoretogram showing the separation of nonphosphorylated and in vitro phosphorylated reporter substrate molecules from a mixture in buffer solution. To obtain the electrophoretic migration standards as shown in FIG. 11A, a dilute mixture of Fl-s PKC, Fl-sPKA, and P-Fl-sPKC, each at approximately 1 nM in concentration, was loaded into capillary 22 by gravitational fluid flow and the loaded volume calculated from Poiseulle's equation. FIG. 11A shows a nonphosphorylated Fl-sPKC peak 136, a nonphosphorylated Fl-sPKA peak 137, and a phosphorylated P-Fl-sPKC peak 138 as standards.

Technical Aspects of Measurements in FIGS. 2A–C

In the measurements illustrated by FIGS. 2A–C, prior to mounting on the microscope stage for microinjection and analysis at room temperature (20°–23° C.), each cell chamber 199 was treated by addition of 10 μl of 10 mM Pefabloc (Boehringer-Mannheim, Indianapolis, Ind.) in buffer A with gentle manually pipetted mixing using a Pipetman® (Rainin, Woburn, Mass.).

This yielded a final Pefabloc concentration of 200 μM. Pefabloc is a soluble, physiologically tolerated, inhibitor of serine proteases, a subset of intracellular enzymes that tend to degrade peptides. Pefabloc was included to minimize intracellular degradation of Fl-sPKC. In instances where PKC was to be activated, as in FIG. 2C, 10 μl of 5 μM phorbol myristic acid (PMA, purchased from Sigma, St. Louis, Mo.) freshly diluted from a 200 μM stock solution, into buffer A, was added and mixed gently at the same time as Pefabloc. The stock solution was composed of PMA dissolved in dimethyl sulfoxide (DMSO). The cell chambers 199 were returned to the incubator (37° C., 5% $CO_2$), for 5 minutes. Immediately after mounting on the microscope stage 30, the culture medium in the cell chamber 199 was replaced by continuous flow and removal (2 ml/min, approximately four cell chamber volumes/min) of room temperature (20°–23° C.) buffer A with added 10 mM glucose and 200 μM Pefabloc. Flow was maintained throughout microinjection and recovery. This typically lasted 20–30 minutes. Flow was halted briefly during lysis, restarted 1 minute after lysis and capillary loading and continued throughout the course of electrophoresis.

In the measurements illustrated by FIGS. 2A–C, Fl-sPKC was diluted in buffer B, a physiologically compatible intracellular buffer composed of 10 mM Hepes and 140 mM KCl, at pH 7.4. The final concentration of Fl-sPKC was ~800 μM. Mixed with the Fl-sPKC was Calcium Orange (Molecular Probes, Eugene, Oreg.) at a concentration of 500 μM. This mixture was microinjected into several cells in the same cell chamber through a Femtotip I glass microinjection needle 116 with an Injectman 5171 micromanipulator and a Transjector 5346 system at a pressure of 80 hPa for 0.2 sec (Femtotip, Injectman and Transjector are products of Eppendorf, Hamburg, Germany). The intracellular concentrations are estimated to be 8 μM Fl-sPKC and 5 μM Calcium Orange. The injection was performed on the same microscope 12 as used for cell selection and analysis, namely an Axiovert 135 (Zeiss). The cells 46 that had been successfully microinjected were identified by visual observation of internal Calcium Orange epi-fluorescence through a set of TRITC filters (Chroma Technology Corp., Brattleboro, Vt.) (not shown, but included in the microscope 12) to minimize photodestruction of the fluorescein moiety on Fl-sPKC. Only the cells 46 that appeared healthy as judged by the presence of a uniformly fluorescent, homogeneous cytoplasm and smooth plasma membrane, were chosen for analysis. A large fraction of microinjected cells failed this requirement, demonstrating membrane defects, punctuate fluorescence, or excessively bright nuclei.

Results of Measurements in FIGS. 2A–C

FIG. 2B is the graph of an electrophoretogram showing the separation from the contents of a rat basophilic leukemia (RBL) cell 46 in which the enzyme protein kinase C (PKC) was not specifically activated (peak 144 at ~1200 sec. is thought to be a byproduct of intracellular proteolysis). In particular FIG. 2B is an electrophoretogram of the contents of an RBL cell 46 that was microinjected, as described above, in the absence of an extracellular stimulant. FIG. 2B shows a sizable nonphosphorylated fluorescent peak 140 that corresponds in migration time to Fl-sPKC peak 136 shown in FIG. 2A. In contrast, only a very small peak 142 that corresponds in migration time to phosphorylated P-Fl-s PKC is observed. Virtually no net intracellular PKC activity occurred within the treated cell 46 from the time of microinjection.

FIG. 2C is the graph of an electrophoretogram showing the separation from the contents of an RBL cell 46 in which PKC was specifically activated by treatment with 100 nM phorbol myristic acid (PMA). In contrast to the results of FIG. 2B, the electrophoretogram in FIG. 2C of the contents of an RBL cell 46 exposed to the extracellular, membrane permeant stimulant, PMA shows evidence of significant net PKC activity. The peak 146 corresponding to Fl-sPKC and the peak 148 corresponding to P-Fl-sPKC are of nearly equal magnitude.

Clearly activation of an intracellular kinase by a potent pharmacologic activator can be measured by this approach. Furthermore, both electrophoretograms in FIGS. 2B and 2C show the presence of peaks that cannot be readily identified. It is believed that these peaks correspond to forms of Fl-sPKC that have been partially degraded by intracellular proteases or covalently modified by other intracellular non-kinase enzymes. The occurrence of these molecular products as discrete, well defined peaks suggests that they represent discrete molecular species and are the products of a limited number of specific side reactions. The Fl-sPKC molecules are not overwhelmingly consumed by these side reactions, since in both FIGS. 2B and 2C, side products account for only about 50% of collected fluorescence. The unique species that migrates most slowly in FIG. 2C indicated as a peak 152 may correspond to a modified version of P-Fl-sPKC.

Technical Aspects of Measurements in FIGS. 3A–C

FIG. 3A is the graph of an electrophoretogram showing the separation of nonphosphorylated and in vitro phosphorylated reporter substrate molecules from a mixture in buffer solution, to be viewed as a reference for the electrophoretic mobilities of both species. FIG. 3B is the graph of an electrophoretogram showing the separation from the contents of a rat basophilic leukemia (RBL) cell 46 in which the enzyme protein kinase C (PKC) was not specifically activated. FIG. 3C is the graph of an electrophoretogram showing the separation from the contents of an RBL cell 46 in which PKC was activated as a consequence of treatment of the cell with extracellular ATP.

In the measurements illustrated by FIGS. 3A–C the sequence of events is as follows. First, the cell chamber 199 was removed from an incubator, the culture medium replaced with two manually pipefted exchanges of buffer A containing additional 10 mM glucose, and the cells 46 within the chamber 199 microinjected, as described above, with a mixture of 100 μM Fl-sPKC and 500 μM rhod-2 (Molecular Probes, Eugene, Oreg.) in buffer B. The intracellular concentrations are estimated to have been 1 μM Fl-sPKC and 5 μM rhod-2. The chamber 199 was then placed back in the incubator (37° C., 5% $CO_2$) for 15 minutes. After this recovery period all further manipulations occurred at room temperature (20°–23° C.). The buffer within the cell chamber 199 was replaced with five exchanges of manually pipetted buffer A containing additional 10 mM glucose and placed back on the microscope stage for cell selection and analysis. The cells 46 that had been successfully microinjected were identified by visual observation of internal rhodamine epi-fluorescence through a set of TRITC filters (Chroma) in order to minimize photodestruction of the fluorescein moiety on Fl-sPKC. Only those cells of the cells 46 that appeared healthy as judged by the presence of a uniformly fluorescent, homogeneous cytoplasm and smooth plasma membrane, were chosen for analysis. As described previously, a large fraction of the microinjected cells failed this requirement, demonstrating membrane defects, punctuate fluorescence, or excessively bright nuclei.

Figure 10:
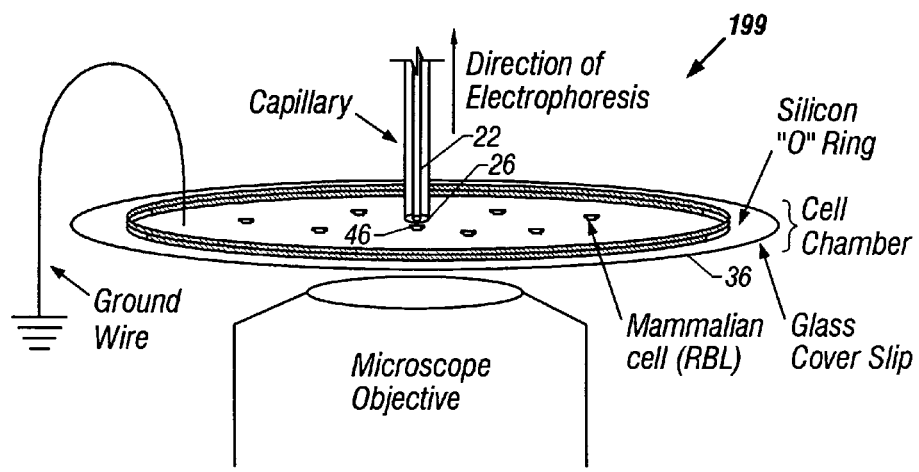
FIG. 10 is a diagrammatic depiction of the cell chamber, holding mammalian cells and electrophoresis buffer, used in conjunction with the fast lysis apparatus in the illustrated embodiment.

In instances where PKC was to be activated, as in FIG. 3C, 10 μl doses of 500 μM adenosine triphosphate (ATP, Sigma, St, Louis, Mo.) in buffer A were pipetted manually directly above the cell of interest. RBL-2H3 cells 46 express transmembrane purinergic receptors on their surface. When these receptors bind ATP, an intracellular G-protein linked signal transduction cascade becomes activated that can give rise to intracellular PKC activation. Finally, after cell selection and either no further treatment, as in FIG. 3B, or treatment with ATP, as in FIG. 3C, lysis was triggered by manual firing the Nd:YAG laser 18 and electrophoresis started simultaneously as described above.

Results of Measurements in FIGS. 3A–C

FIG. 3B is an electrophoretogram of the contents of an RBL cell 46 that was microinjected, as described above, and received no treatment with ATP. The distribution of fluorescent peaks is very similar to that seen in FIG. 2B. The peak 154 that corresponds to Fl-sPKC is six times greater in area than the peak 156 that corresponds to P-Fl-sPKC. This indicates that six-fold more of the reporter substrate was nonphosphorylated as compared to phosphorylated. In the absence of treatment to activate PKC, as in FIG. 2B, the net activity of PKC is low.

FIG. 3C is an electrophoretogram of the contents of an RBL cell 46 that was similarly microinjected, but subsequently exposed to two doses of ATP. The doses were administered 3 minutes apart with the last dose being added about 2 minutes prior to lysis. FIG. 3C demonstrates that a nearly 1:1 ratio of Fl-sPKC integrated under the peak 158 and P-Fl-sPKC integrated under the peak 160 occurred within the cell 46 following extracellular treatment with ATP, a physiological activator of PKC.

Figure 11B:
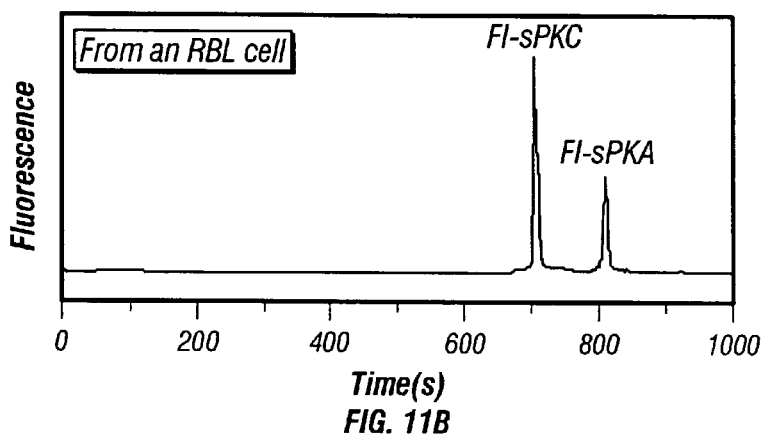
Figure 11C:
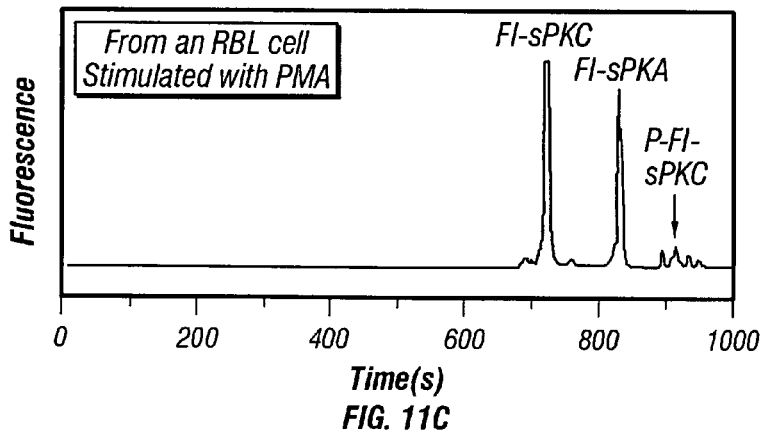

Technical Aspects of Measurements in FIGS. 11A–C

FIG. 11A is the graph of an electrophoretogram showing the separation of nonphosphorylated and in vitro phosphorylated reporter substrate molecules from mixture in buffer solution, to be viewed as a reference for the electrophoretic mobilities of each species, Fl-sPKC, Fl-sPKA, and P-Fl-s PKC. At the time of this analysis, no in vitro phosphorylated P-Fl-sPKA was available for use as a migration standard. FIG. 11B is the graph of an electrophoretogram showing the separation from the contents of an RBL cell 46 in which the enzymes PKC and protein kinase A (PKA) were not specifically activated. FIG. 11C is the graph of an RBL cell 46 in which PKC was activated as a consequence of treatment of the cell with extracellular PMA.

In the measurements illustrated by FIGS. 11B–C, the following compounds were mixed in buffer B: FL-sPKC at 120 μM, Fl-sPKA at approximately 100 μM, and Calcium Orange (Molecular Probes, Eugene, Oreg.) at 650 μM. The mixture was microinjected at room temperature (20°–23° C.) into several cells in the same cell chamber through a Femtotip I glass microinjection needle 116 (Eppendorf, Hamburg, Germany) with a Micromanipulator 5171 and Transjector 5246 system (Eppendorf) at a pressure of 80 hPa for 0.2 sec. The intracellular concentrations are estimated to be 1.2 μM Fl-sPKC, 1 μM Fl-sPKA, and 6.5 μM Calcium Orange. The injection was performed on the same microscope 12 as used for cell selection and analysis, namely an Axiovert 135 (Zeiss). The cells 46 that had been successfully microinjected were identified by visual observation of internal Calcium Orange epi-fluorescence through a set of TRITC filters (Chroma Technology Corp., Brattleboro, Vt.) (not shown, but included in the microscope) to minimize photodestruction of the fluorescein moiety on the reporter substrate molecules. Only the cells that appeared healthy as judged by the presence of a uniformly fluorescent, homogeneous cytoplasm and smooth plasma membrane, were chosen for analysis. A large fraction of microinjected cells failed this requirement, demonstrating membrane defects, punctate fluorescence, or excessively bright nuclei.

In cases where the cells were to be stimulated with PMA as in FIG. 11C, prior to injection, the culture media in the cell chamber 199 was replaced by a solution of 1 μM PMA in buffer A containing 10 mM glucose. The cell chamber was returned to the incubator (37° C., 5% $CO_2$) for 10 minutes.

In all cases, immediately after removal from the incubator, the cell chambers 199 were mounted on the microscope stage 30 and the solution in the cell chamber was replaced by continuous flow and removal (2 ml/min, approximately four cell chamber volumes/min) of room temperature buffer A with added 10 mM glucose. Flow was maintained throughout microinjection and recovery. This typically lasted 5–15 minutes. Flow was halted briefly during lysis, restarted within 1 minute after lysis and capillary loading and continued throughout the course of electrophoresis.

Results of Measurements in FIGS. 11A–C

FIG. 11B is the graph of an electrophoretogram showing the separation from the contents of an RBL cell 46 in which the enzymes PKC and PKA were not specifically activated. In particular FIG. 11B is an electrophoretogram of the contents of an RBL cell that was microinjected, as described above, in the absence of extracellular PMA. FIG. 11B shows sizable peaks that correspond in migration times to Fl-sPKC and Fl-sPKA. No peaks that could be positively identified as the phosphorylated forms, P-Fl-sPKC or P-Fl-sPKA, of the reporter substrate peptides occurred in this trace. No measurable net intracellular PKC or PKA activity occurred within the cell 46 from the time of microinjection.

FIG. 11C is the graph of an electrophoretogram showing the separation from the contents of an RBL cell 46 in which the enzyme PKC was specifically activated with PMA. PMA is well characterized as a specific activator of PKC but not of PKA. As described above, this cell was microinjected after treatment with PMA. FIG. 11C shows sizable peaks that correspond in migration times to Fl-sPKC, Fl-sPKA, and a cluster of smaller peaks centered with a migration time that matches the phosphorylated form of Fl-sPKC, P-Fl-s PKC. All three chemical species separated from a mixture in buffer in FIG. 11A are shown separated from the contents of a small mammalian cell in FIG. 11C. Since a migration standard for the phosphorylated form of Fl-sPKA was not available at the time of this measurement, it is uncertain if any of these peaks correspond to P-Fl-sPKA. As noted above, in the absence of stimulation with PMA, none of the peaks in the cluster centered around 910 seconds are seen at comparable magnitude. A small, but measurable amount of PKC activation has occurred within the cell analyzed in FIG. 11C.

Figure 12:
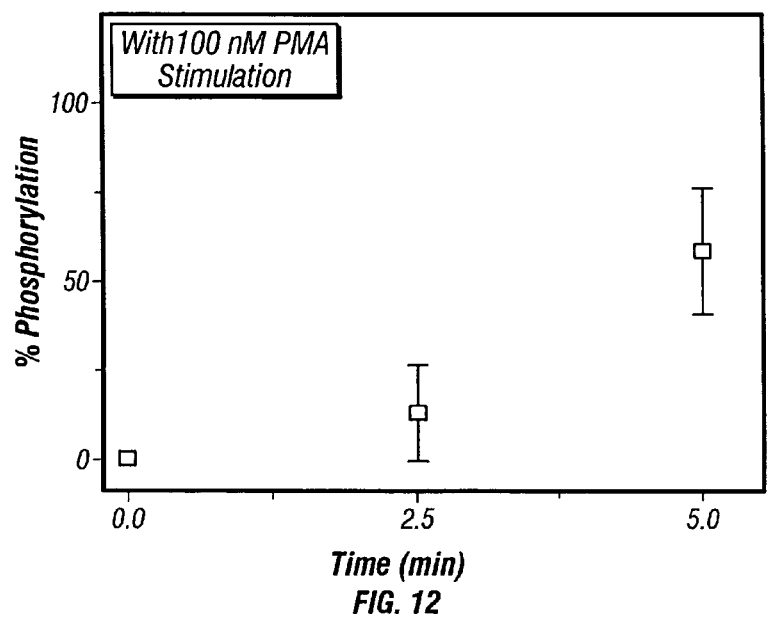
FIG. 12 is a graph of the percentage of phosphorylation as a function of time showing the intracellular phosphorylation of a reporter substrate, in individual murine fibroblast NIH/3T3 cells, in response to extracellular treatment with a potent pharmacologically specific activator of PKC.

Technical Aspects of the Measurements in FIG. 12

FIG. 12 is a graph of degree of phosphorylation as a function of time showing the course of intracellular phosphorylation of reporter substrate by PKC in response to extracellular treatment of murine NIH/3T3 cells with 100 nM PMA, a potent and specific pharmacological activator of PKC. Each point represents the average of three or more measurements, and the error bars represent a single standard deviation.

In the measurements illustrated in FIG. 12 FL-sPKC at 300 μM and Calcium Orange (Molecular Probes, Eugene, Oreg.) at 900 μM were mixed in buffer B. The mixture was microinjected at room temperature (20°–23° C.) into several cells in the same cell chamber through a Femtotip I glass microinjection needle 116 (Eppendorf, Hamburg, Germany) with a Micromanipulator 5171 and Transjector 5246 system (Eppendorf) at a pressure of 80 hPa for 0.2 sec. The final intracellular concentrations are estimated to have been 3 μM for Fl-sPKC and 9 μM for Calcium Orange. Following microinjection, the cells 46 were allowed to recover at room temperature for 10–15 minutes on the microscope stage 30 with continuous flow (2 ml/min) of buffer A with added 10 mM glucose.

In cases where PKC was to be stimulated, PMA was diluted from a stock solution in dimethyl sulfoxide (DMSO) into buffer A containing additional 10 mM glucose immediately prior to use. This solution (approximately 500 μl) was exchanged for the solution within a cell chamber 199 manually with a hand-held Pipetman® (Rainin Instrument Co., Woburn, Mass.). This was carried out while the cell chamber 199 was mounted on the microscope stage 30 after the flow of exchange buffer had been paused. The flow of buffer was halted throughout the time of incubation with PMA containing solution. During the time of PMA stimulation, a healthy cell was selected by observation of Calcium Orange epi-fluorescence. At the appropriate time point, either after 2.5 or 5 minutes, the cell was lysed by remote triggering of the Nd:YAG laser 18 and loaded into the inlet 26 of the capillary 22 by the simultaneous start of electrophoresis.

The peak areas corresponding to Fl-sPKC and P-Fl-sPKC were measured using the software analysis package Origin 5.0 (Microcal Software, Inc., Northampton, Mass.).

Results of Measurements in FIG. 12

FIG. 12 is a graph of degree of phosphorylation as a function of time showing the time course of intracellular phosphorylation of reporter substrate by PKC in response to extracellular treatment of murine NIH/3T3 cells with PMA, a potent and specific activator of PKC. FIG. 12 shows the quantitative results of a number of measurements conducted to determine the time course of intracellular reporter substrate phosphorylation in NIH/3T3 cells in response to activation by exposure to 100 nM PMA at room temperature (20°–23° C.). From the approximate correspondence of the 5 minute time point to the 50% phosphorylation level, a rate of Fl-sPKC phosphorylation of 6+/−2 nM/s is estimated to occur within NIH/3T3 cells under these conditions. At this rate, only 0.007% of the reporter substrate peptide would have been phosphorylated in the conservatively estimated 33 msec interval between laser induced cell lysis and the initiation of electrophoretic separation. Thus, the rapidity with which the contents of a cell are obtained and separated allows for exceptionally accurate snapshots of intracellular chemical reactions to be obtained. FIG. 12 further demonstrates that measurements can be made from a second mammalian cell type, namely NIH/3T3 cells, as well as from RBL cells.

Conditions and Results Unique to the Second Embodiment

Summary

In the second embodiment, illustrated by FIGS. 4A–8B *Xenopus laevis* frog oocytes 46' were used as cells of interest. In the measurements of PKC activation, illustrated by FIGS. 4A–6B, Fl-sPKC was microinjected into an oocyte 46'. Cytoplasm (~22 pl) from the oocyte 46' was then loaded into the capillary 22 and electrophoresed. Fl-sPKC and P-Fl-sPKC were separated and quantified from their fluorescence. The ratio of P-Fl-sPKC to Fl-sPKC measures the relative activation of PKC, i.e. the intracellular balance between PKC and the phosphatases. Phosphatases catalyze the reverse of the reaction catalyzed by kinases—namely the removal of a phosphate from a substrate molecule.

Figure 7:
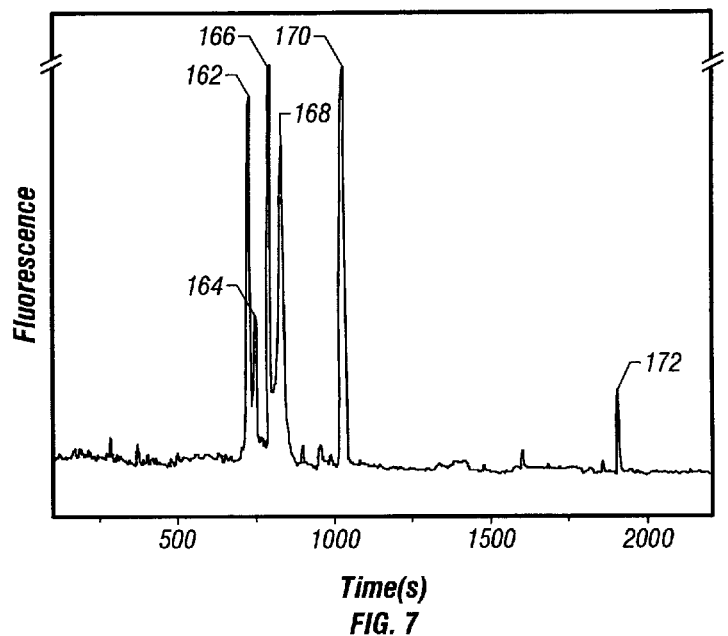
FIG. 7 is an electrophoretogram showing the separation of three different specific kinase reporter substrates from a sample of the contents of a Xenopus oocyte that had been previously microinjected.

FIG. 7 is a graph of phosphorylation as a function of time showing the separation of three different specific kinase reporter substrates from a sample of the contents of a *Xenopus laevis* oocyte 46' that had been previously microinjected to contain ~1⊠M Fl-sPKC, ~330 nM Fl-sPKA, and ~10 nM Fl-scdc2K. Fl-sPKA, a specific reporter for protein kinase A (PKA) activity has the sequence FL-Lys-Arg-Arg-Glu-Ile-Leu-<u>Ser</u>-Arg-Arg-Pro-Ser-Tyr-Arg (sequence ID NO:1), and was derived from the CREB protein. Fl-scdc2K, a specific reporter for cdc2 kinase (originally identified genetically as cell division cycle mutant 2) has the sequence Fl-Gly-Gly-Gly-Arg-Ser-Pro-Gly_Arg-Arg-Arg-Arg-Lys (sequence ID NO:2), and comprises a consensus phosphorylation site derived from several proteins. The underlined serine residues are the sites of phosphorylation. The peptides were synthesized and labeled with fluorescein as described for Fl-sPKC, except that Fl-scdc2K was labeled with the mixed 5- and 6-isomers of carboxyfluorescein succinimidyl ester (100–200 mg/ml, Molecular Probes, Eugene Oreg.); thus, Fl-scdc2K consisted of two isomeric forms. A peak 162 and a peak 172 were identified by their migration times as observed when injected into oocytes 46' singly (not shown). The first doublet, peaks 162 and 164, corresponds to two isomers of either phosphorylated or nonphosphorylated Fl-scdc2K. The second doublet, peaks 166 and 168, corresponds to two isomers of the other form of Fl-scdc2K. One peak 170 represents nonphosphorylated Fl-sPKC, and one peak 172 represents nonphosphorylated Fl-sPKA.

As shown in FIG. 7, when a plurality or mixture of peptides of different kinase specificities was loaded into the oocyte 46', each of the different peptides could be detected. This demonstrates that from a single oocyte 46', it is possible to quantify simultaneously the activation of multiple kinases within a single pathway or in different pathways, making this technique a powerful tool to study cellular signal transduction cascades.

Cells Used

Oocytes 46' were surgically obtained from pigmented or albino *Xenopus laevis* frogs and were cultured as described previously. Oocytes 46' were microinjected by means of an injector mounted on a low power dissecting microscope (not shown) with 50 nl of reporter substrate peptide (0.5–200 µM) in buffer B, and then incubated for 30 min to permit diffusion of the peptide through the oocyte 46'. For measurements, oocytes 46' were placed in buffer C (96 mM NaCl, 2 mM KCl, 1.8 mM $CaCl_2$, 1 mM $MgCl_2$, 5 mM Hepes, pH 7.6). When LPA (1-oleoyl-2-hydroxy-sn-glycero-3-phosphate, Avanti Polar Lipids, Alabaster, Ala.) was added to the oocytes 46', fatty acid-free bovine serum albumen (5%) was used as a carrier as described previously.

Separation Conditions

Figure 8A:
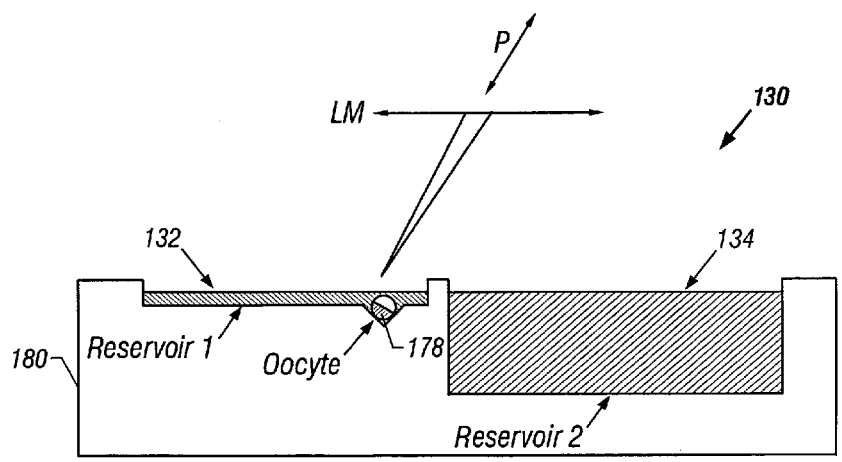
FIGS. 8A and 8B are diagrammatic depictions of the components of the apparatus used to make measurements of intracellular enzyme activity.
Figure 8B:
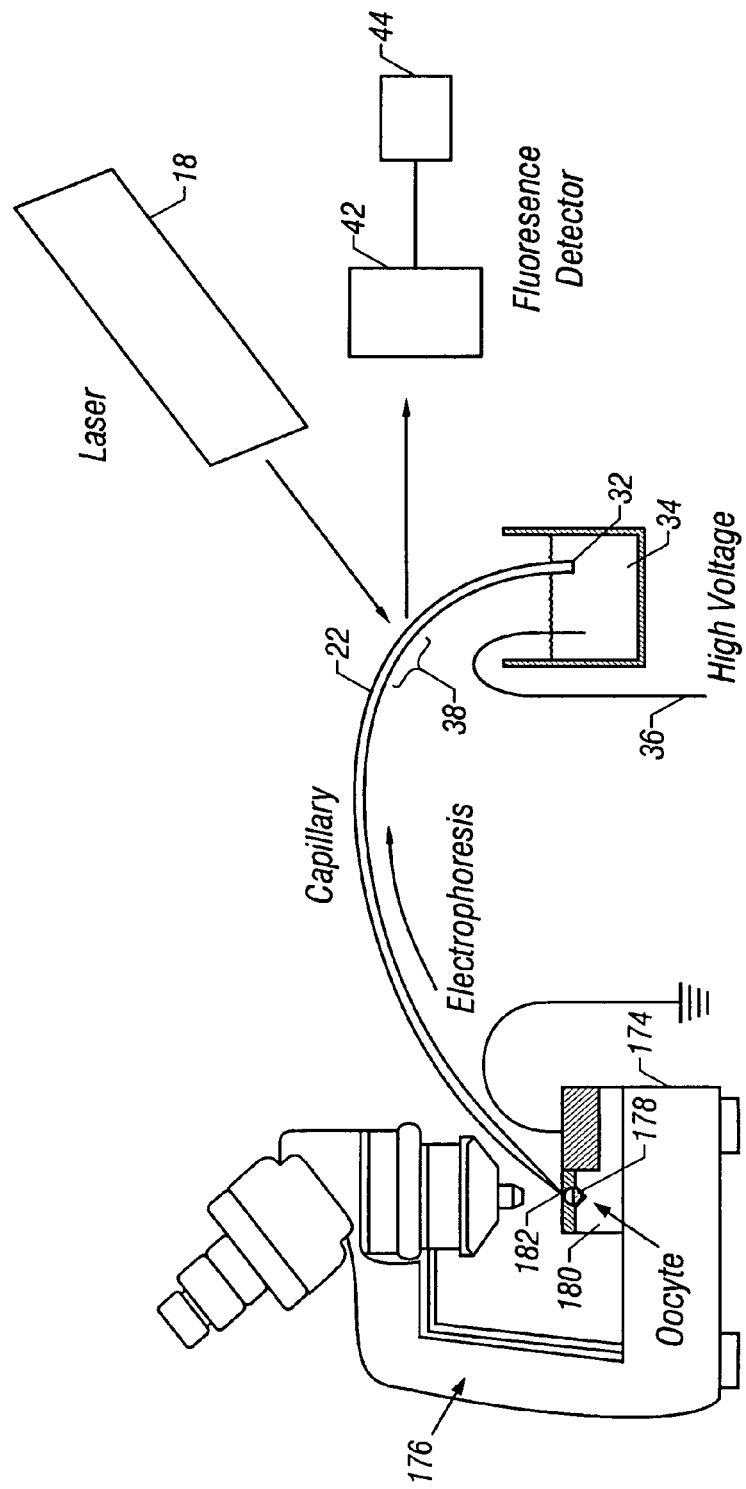

All samples from the oocytes 46' were obtained and electrophoresed by a method referred to as piezoelectric sampling/rapid translation/capillary electrophoresis (PERT CE). The apparatus used for PERT CE is illustrated in FIGS. 8A–B. FIGS. 8A and 8B are diagrammatic depictions of the components of the apparatus used to make measurements of intracellular enzyme activity from single *Xenopus laevis* oocytes 46'. FIG. 8A shows a custom designed holder 130 for the oocyte 46' and an electrophoresis buffer. The holder is part of a complete apparatus for automatically sampling oocyte cytoplasm and rapidly subjecting this sample to electrophoresis before any substantial change in the substrate molecules can occur. This is achieved by providing a sharpened electrophoresis capillary 22 attached to a high speed translation system to plunge the capillary into the cell to capture a "plug of cytoplasm". Then the capillary is automatically withdrawn from the oocyte and rapidly moved to make electrical contact with a reservoir 134 of electrophoresis buffer so that electrophoresis of the substrate molecules within the "plug" commences before any additional chemical reactions occur. In the preferred device a piezoelectric element mover the capillary up and down (vertical axis) to sample the cell while a linear motor rapidly moves the capillary in a horizontal direction to transition from the oocyte to the reservoir 132.

In FIG. 8A the arrows show the axes of movement of the capillary 22 by the piezoelectric element P and linear motor LM. A reservoir 132 with the oocyte 46' contains a biologically compatible buffer C (96 mM NaCl, 2 mM KCl, 1.8 mM $CaCl_2$, 1 mM $MgCl_2$, 5 mM Hepes, pH 7.6), while the second reservoir 134 contains the electrophoresis buffer. FIG. 8B shows a schematic of microscope, capillary, and fluorescence detection similar to FIG. 9. The holder 130 of FIG. 8A was mounted on the stage 174 of an upright microscope 176 or below a dissecting microscope. For simplicity, the piezoelectric element and linear motor are not shown. The oocyte 46' is placed in a "V"-shaped well in the reservoir 132 that had been drilled into a block of Teflon or polycarbonate 180. The reservoir 132 was filled with the biologically compatible buffer, buffer C. A tip 182 of the separation capillary 22 (50 µm I.D., 360 µm O.D.) was etched to an outer diameter of ~70 µm by treatment with hydrofluoric acid. The capillary tip 182 was mounted on the edge of a piezoelectric motor element (Piezo Systems, Cambridge, Mass. not shown) to allow controlled vertical movement of the tip 182 indicated by direction P in FIG. 8A. A micromanipulator (not shown) which held the piezoelectric device and the capillary 22 was mounted on a linear motor (not shown) to allow controlled horizontal movement indicated by direction LM in FIG. 8A. Using the micromanipulator, the etched tip of the capillary 22 was placed above and adjacent to the oocyte's plasma membrane.

To obtain cytoplasm, the capillary 22 was driven 60 µm into the oocyte 46' by the piezoelectric element. This resulted in the filling of the tip 182 of the capillary 22 with a "plug" of sampled cytoplasm. The capillary 22 was then automatically withdrawn from the cytoplasm. Immediately after withdrawing of the capillary 22 from the oocyte 46', the capillary 22 was moved horizontally (1.2 cm at a velocity of 6 cm/s) by the linear motor and then rapidly lowered by the piezoelectric element into a second reservoir 134 that contained an electrophoresis buffer. Electrophoresis was initiated immediately. This entire sequence was computer controlled and accomplished in 350 ms. The linear motor (Oriental Motor Co., Torrance, Calif.) was controlled by a solid state relay board and an analog output board (Keithley, Cleveland, Ohio) (not shown).

Electrophoretic separations from oocyte cytoplasm were carried out under two distinct sets of conditions. In the measurements illustrated in FIGS. 4A–D, capillaries with a proprietary neutral coating (Supelco, Bellefonte, Pa.) were used. In the measurements illustrated in FIGS. 5 and 6A–B, polyethyleneimine (PEI) coated capillaries were used and prepared as follows. Fused silica capillaries 22 (Polymicro Technologies, Phoenix, Ariz.) were washed continuously for 30 min with 1 M NaOH or KOH followed by a 15-min wash with water. The capillaries 22 were then coated either by flowing PEI (5%) continuously through each capillary 22 for 60 min. or by loading each capillary 22 with PEI (5%) and then incubating the PEI-loaded capillary for 60 min. The solution of PEI was expelled from the capillary 22 with nitrogen. Each capillary 22 was rinsed with water for 15 min and then with the electrophoresis buffer for 15 min.

All electrophoretic separations shown in FIGS. 4A–7 are best understood as examples of the use of micellar electrokinetic chromatography (MEKC). This terminology refers to the use of an electrophoretic buffer in which detergent micelles are used to facilitate reproducible and efficient separations. The use of micelles in these separations has proven necessary because *Xenopus* oocyte cytoplasm contains relatively large amounts of amphiphilic molecules, particularly in the form of the highly negatively charged protein phosvitin. Electrophoresis was performed in a 50–100 cm long capillary 22 (360 µm outer diameter, 50 µm internal diameter). The electrophoretic voltage was 10–15 kV (current, 30–60 pA). The electrophoresis was performed in buffer D (45 mM NaCl, 1.6 mM KCl, 0.6 mM $MgCl_2$, 1% triton-X 100, and 10 mM Hepes (pH 7.4)), or buffer E (buffer D with 645 mg/ml cholic acid). Between electrophoretic runs, the capillary 22 was washed for 25 min with the electrophoresis buffer. The fluorescence of analyte bands migrating through the capillary 22 was measured 15–25 cm from the outlet end of the capillary 22 as previously described. Peptide standards were loaded into the capillary 22 by gravitational fluid flow and the loaded volume calculated from Poiseulle's equation.

Detection

For detection purposes, a 5 mm length of the polyimide coating was removed from the outer surface of the capillary 22 at a position 50 cm from the inlet tip 182. The coating was removed by brief heating with a disposable butane lighter and was subsequently cleaned with a 70% ethanol solution. Through this optical window 38, the capillary lumen was interrogated by the focused beam of an argon ion laser (operated at 488 nm) (Uniphase, San Jose, Calif.). Fluorescence was collected at a right angle to the capillary 22 and laser beam by a collecting lens (not shown), and the light was measured with a R928 photomultiplier tube (PMT) (Hammatsu, Bridgewater, N.J.) (not shown) with a 533DF56 spectral filter (Omega Optical, Brattleboro, Vt.) (not shown). The photomultiplier tube current was amplified and converted to a voltage with a preamplifier (not shown, but included in the detector 42). The signal was digitized by a data acquisition board (DAS-1802ST-DA or DAS-1802HR-DA, Keithly Metrabyte, Taunton, Mass.) in a personal computer 44 (Gateway, Sioux City, S.Dak.). The data were plotted and peak areas calculated using Origin (Microcal, Northhampton, Mass.). The detection limit of this configuration was approximately $10^{-19}$ moles, about 60,000 molecules, well below the detection limit for physiologically relevant measurement (see Table 1).

Technical Aspects of the Measurements in FIGS. 4A–D

Figure 4B:
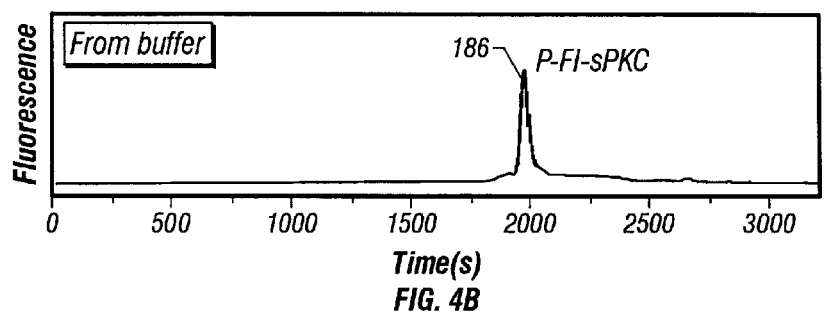

FIG. 4A is the graph of an electrophoretogram that shows the mobility of the nonphosphorylated form of the reporter substrate in buffer at a peak 184. FIG. 4B is the graph of an electrophoretogram that shows the mobility of the phosphorylated form of the reporter substrate in buffer at a peak 186. In FIGS. 4A and 4B, reporter substrate standards were loaded into the capillary 22 by gravitational fluid flow and the loaded volume calculated from Poiseulle's equation. In the measurements illustrated in FIGS. 4C and 4D, individual oocytes 46' were microinjected with 50 nl of 200 µM Fl-sPKC as described and incubated in buffer C for 30 minutes to allow diffusion of the reporter substrate. The estimated final intracellular concentration of reporter substrate was ~10 µM. Separations were achieved with PERT CE sampling followed by MEKC with buffer E through a capillary with a proprietary neutral inner coating (Supelco, Bellefonte, Pa.). In the measurements, the reservoir 132 that contained the oocyte 46' was filled with buffer C, while the capillary 22, the second reservoir 134 that served as the inlet for electrophoresis and the output reservoir 34 contained buffer E.

Results of Measurements in FIGS. 4A–D

Figure 4C:
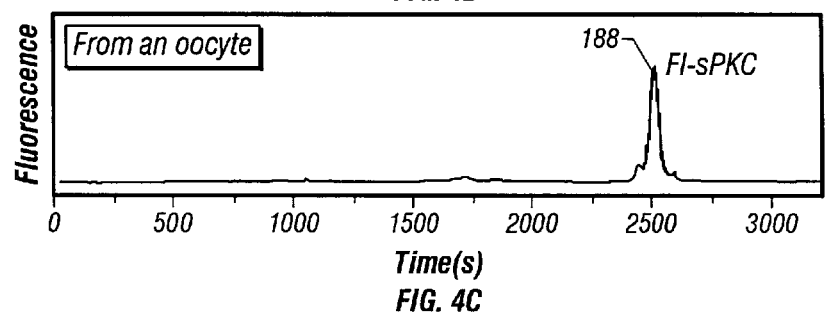

FIG. 4C is the graph of an electrophoretogram that shows the separation of a sample of the contents of a *Xenopus laevis* oocyte that had been previously microinjected to contain ~10 µM reporter substrate. In this case, the oocyte 46' was not treated to activate intracellular PKC. FIG. 4C is an electrophoretogram of a sample of cytoplasm from the oocyte 46' that was not treated with an extracellular stimulant. Essentially all collected fluorescence at the peak 188 corresponded to nonphosphorylated Fl-sPKC, as can be seen by reference to the peak 184 of FIG. 4A, which is an electrophoretogram of Fl-sPKC loaded from buffer.

Figure 4D:
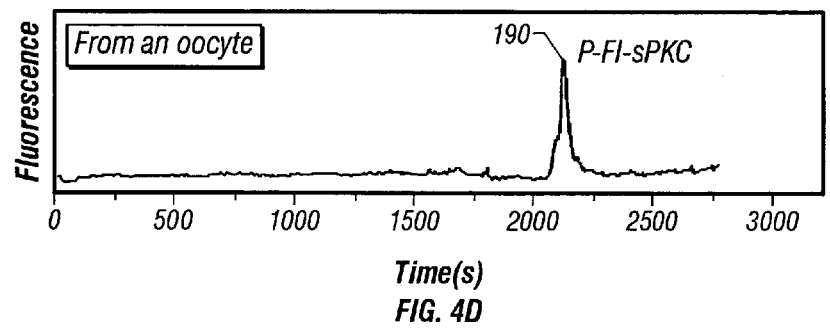

FIG. 4D is the graph of an electrophoretogram that shows the separation of a sample of the contents of a *Xenopus laevis* oocyte that had been previously microinjected to contain ~10 µM reporter substrate. In this case, the oocyte 46' was treated extracellularly with 10 µM PMA for 10 minutes prior to sampling to specifically activate intracellular PKC. FIG. 4D is an electrophoretogram of a sample from the a oocyte 46' that was exposed to 10 µM PMA for 10 minutes. In this case, essentially all collected fluorescence at the peak 190 corresponded to P-Fl-sPKC as can be seen by reference to the peak 186 of FIG. 4B, an electrophoretogram of P-Fl-sPKC loaded from buffer.

These results demonstrate that net activation of PKC in response to the potent phamacologic stimulant PMA can be measured from a single *Xenopus* oocyte. Further, this shows that in the absence of stimulation, net PKC activity is relatively low in oocytes.

Figure 5:
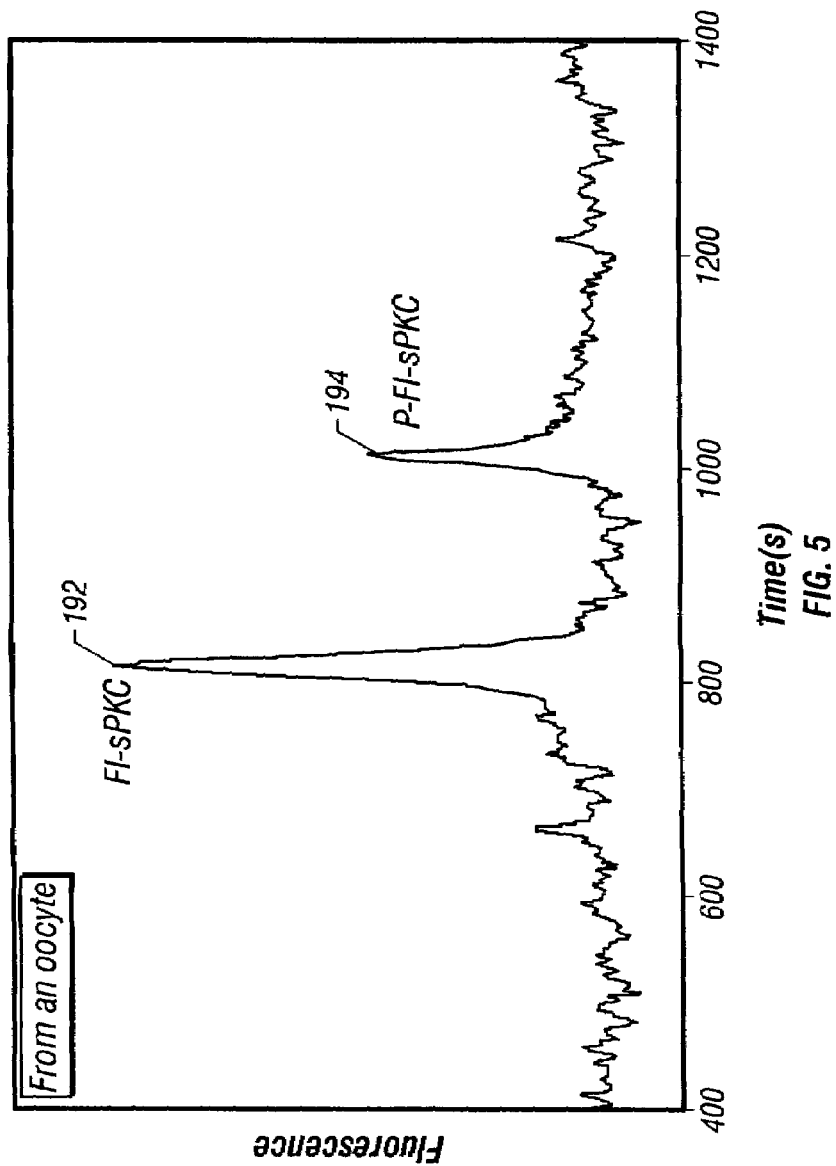
FIG. 5 is an electrophoretogram showing the separation of a sample of the contents of a Xenopus oocyte that had been previously microinjected to contain a reporter substrate. The oocyte was treated to show an intermediate degree of activation.
Figure 6A:
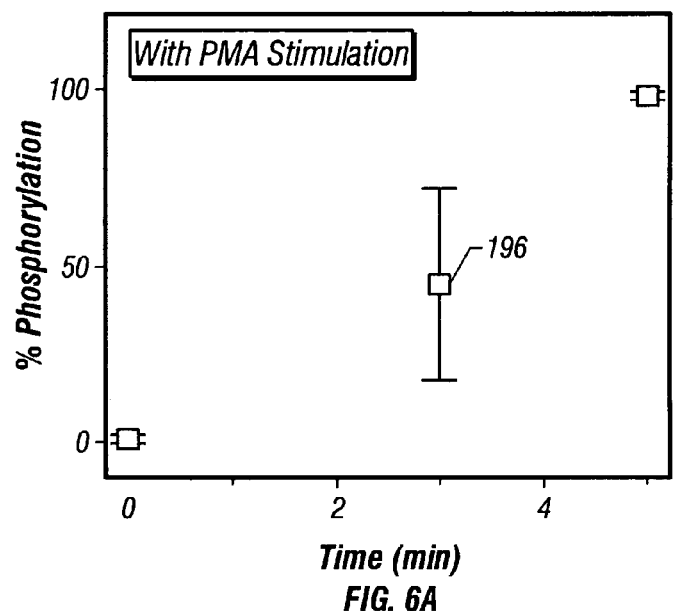
FIG. 6A is a graph of the percentage of phosphorylation as a function of time showing the intracellular phosphorylation of a reporter substrate in response to extracellular treatment with a potent pharmacologic specific activator.
Figure 6B:
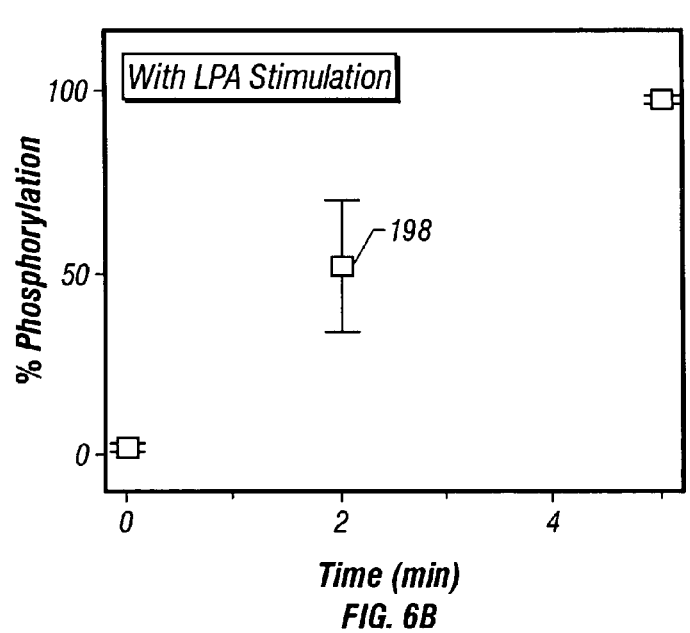
FIG. 6B is a graph of phosphorylation as a function of time showing the time course of intracellular phosphorylation of reporter substrate in response to extracellular treatment of Xenopus oocytes with a physiological activator.

Technical Aspects of the Measurements in FIGS. 5 and 6A, 6B

FIG. 5 is a graph of fluorescence as a function of time showing the separation of a sample of the contents of a *Xenopus laevis* oocyte 46' that had been previously microinjected to contain ~10 µM reporter substrate. In this case, the oocyte 46' was treated with 10 µM PMA for 3 minutes prior to sampling to specifically activate intracellular PKC. Both the nonphosphorylated and phosphorylated forms of the reporter substrate are present, indicating that substrate turnover was incomplete after three minutes.

FIG. 6A is a graph of phosphorylation as a function of time showing the time course of intracellular phosphorylation of reporter substrate by PKC in response to extracellular treatment of *Xenopus laevis* oocytes with 10 µM PMA, a potent pharmacologic specific activator of PKC. Each point represents the average of three or more measurements, and the error bars represent a single standard deviation.

FIG. 6B is a graph of phosphorylation as a function of time showing the time course of intracellular phosphorylation of reporter substrate by PKC in response to extracellular treatment of *Xenopus laevis* oocytes with 10 µM LPA (1-oleoyl-2-hydroxy-sn-glycero-3-phosphate, Avanti Polar Lipids, Alabaster, Ala.) a physiological activator of PKC. Each point represents the average of three or more measurements, and the error bars represent a single standard deviation.

In the measurements illustrated in FIGS. 5–7, individual oocytes 46' were microinjected with 50 nl of 200 µM Fl-sPKC as described and incubated in buffer C for 30 minutes to allow diffusion of the reporter substrate. The estimated final intracellular concentration of reporter substrate was approximately 10 µM. Separations were achieved with PERT CE sampling followed by MEKC with buffer D through a capillary with an inner coating of PEI. In the measurements, the reservoir that contained the oocyte 46' was filled with buffer C, while the capillary 22, the second reservoir 134 that served as the inlet for electrophoresis, and the outlet reservoir 34 contained buffer D.

Results of Measurements in FIGS. 5 and 6A, 6B

FIG. 5 is an electrophoretogram of a sample of cytoplasm from an oocyte 46' that was exposed to 10 µM PMA for three minutes. Two fluorescent peaks, peak 192 corresponding to Fl-sPKC and peak 194 corresponding to P-Fl-sPKC, occur. This demonstrates that an intermediate degree of reporter substrate phosphorylation can be measured from a stimulated oocyte.

FIG. 6A is a graph of phosphorylation as a function of time showing the time course of intracellular phosphorylation of reporter substrate by PKC in response to extracellular treatment of *Xenopus laevis* oocytes with a potent pharmacologic specific activator of PKC. FIG. 6A shows the quantitative results of a number of measurements conducted to determine the time course of intracellular reporter substrate phosphorylation in oocytes 46' in response to activation by exposure to 10 μM PMA.

FIG. 6B is a graph of phosphorylation as a function of time showing the time course of intracellular phosphorylation of reporter substrate by PKC in response to extracellular treatment of *Xenopus laevis* oocytes with a physiological activator of PKC. FIG. 6B shows the quantitative results of a number of measurements conducted to determine the time course of intracellular reporter substrate phosphorylation in oocytes 46' in response to activation by exposure to 10 μM LPA. From the intermediate time points, Fl-sPKC was phosphorylated within the oocytes 46' on average at a rate of 25±15 nM/s as shown at a point 196 in FIG. 6A and 43±15 nM/s as shown at a point 198 in FIG. 6B after exposure to PMA and LPA, respectively. At these rates, only ~0.1% of the peptide would have been phosphorylated in the 350 msec interval between the initiation of cytoplasmic sampling and electrophoresis.

Technical Aspects of the Measurement in FIG. 7

FIG. 7 is an electrophoretogram showing the separation of three different specific kinase reporter substrates from a sample of the contents of a *Xenopus laevis* oocyte that had been previously microinjected. In the measurement illustrated in FIG. 7, an individual oocyte 46' was microinjected with 50 nl of a mixture of reporter substrate peptides. The mixture was comprised of 20 μM Fl-sPKC, 7 μM Fl-sPKA, and 500 nM Fl-scdc2K in buffer B. Fl-sPKA, a specific reporter for protein kinase A (PKA) activity has the sequence Fl-Lys-Arg-Arg-Glu-Ile-Leu-Ser-Arg-Arg-Pro-Ser-Tyr-Arg, and was derived from the CREB protein. Fl-scdc2K, a specific reporter for cdc2 kinase (originally identified genetically as cell division cycle mutant 2) has the sequence Fl-Gly-Gly-Gly-Arg-Ser-Pro-Gly-Arg-Arg-Arg-Arg-Lys, and comprises a consensus phosphorylation site derived from several proteins. The underlined serine residues are the sites of phosphorylation. The peptides were synthesized and labeled with fluorescein as described for Fl-sPKC, except that Fl-scdc2K was labeled with the mixed 5- and 6-isomers of carboxyfluorescein succinimidyl ester (100–200 mg/ml, Molecular Probes, Eugene, Oreg.); thus, Fl-scdc2k consisted of two isomeric forms. Each oocyte 46' was incubated in buffer C for 30 minutes to allow diffusion of the reporter substrates. The estimated final intracellular concentrations of reporter substrates were ~1 μM Fl-sPKC, ~330 nM Fl-sPKA, and ~10 nM Fl-scdc2K. Separation was achieved with PERT CE sampling followed by MEKC with buffer D through a capillary with an inner coating of PEI. In the measurement, the reservoir that contained the oocyte 46' was filled with buffer C, while the capillary 22, the second reservoir 134, and the outlet reservoir 34 contained buffer D.

Results of the Measurement in FIG. 7

FIG. 7 shows the separation of three different specific kinase reporter substrates from a sample of the contents of a *Xenopus laevis* oocyte. The peaks were identified by their migration times as observed when injected into oocytes 46' singly (not shown). The first doublet, peaks 162 and 164, corresponds to the two isomeric forms of nonphosphorylated Fl-scdc2K. The second doublet, peaks 166 and 168, corresponds to the two isomeric forms of phosphorylated Fl-scdc2K. Peak 170 is nonphosphorylated Fl-sPKC and peak 172 is nonphosphorylated Fl-sPKA. This measurement demonstrates that the net activities of multiple kinases can be measured from a single oocyte 46'. Further, an exquisite degree of separation is achieved by MEKC in this case as evidenced by the observable separation of isomeric forms of Fl-scdc2K and P-Fl-scdc2K. Finally, this measurement indicates that a substantial degree of cdc2K activity is present in an unstimulated oocyte 46', whereas PKC and PKA remain relatively inactive.

Many alterations and modifications may be made by those having ordinary skill in the art without departing from the spirit and scope of the invention. Therefore, it must be understood that the illustrated embodiments have been set forth only for the purposes of example and that these should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

We claim:

1. A method for measuring an activity of an enzyme in a cell or cellular component thereof, said method comprising:
   inducing or permitting catalysis of a reaction in the cell or cellular component thereof between a labeled substrate and the enzyme, said reaction producing altered labeled substrate;
   disrupting or lysing said cell or cellular component thereof with a laser generated shock wave;
   collecting said labeled substrate, altered labeled substrate, both or portions thereof; and
   determining activity of the enzyme from a comparison of an amount of the altered labeled substrate and an amount of the labeled substrate molecules.

2. The method of claim 1 wherein said collecting is within 33 msec or less of said disrupting or lysing of said cell.

3. The method of claim 1 wherein said collecting is within 1–10 microseconds of said disrupting or lysing of said cell.

4. The method of claim 1 wherein the collecting comprises collecting in an electrophoretic column or channel.

5. The method of claim 1 wherein producing a laser generated shock wave comprises focusing a pulsed laser beam at a position proximate to said cell or cellular component thereof without focusing on said cell or cellular component thereof, and generating said shock wave.

6. The method of claim 1 wherein producing a laser generated shock wave comprises focusing a pulsed laser beam directly in or on said cell or cellular component thereof, and generating said shock wave.

7. The method of claim 6, further comprising defining an opening in said cell of cellular component thereof to lyse only cytoplasmic contents therefrom by said focusing of the pulsed laser beam directly in or on said cell or cellular component thereof.

8. The method of claim 1 wherein said collecting is by fluid flow of said medium.

9. The method of claim 8 wherein said collecting is by siphon fluid flow of said medium.

10. The method of claim 1 wherein said collecting is by electrophoresis through said medium.

11. The method of claim 8 wherein said collecting is by force from said shock wave.

12. The method of claim 8 wherein said collecting is by electroosmotic fluid flow.

13. The method of claim 1 wherein producing a laser generated shock wave is performed at an energy density level just sufficient to split open said cell so that substantially all of said contents of said lysed cell or cellular component thereof and said substrate remain proximate to said lysed cell or cellular component thereof.

14. The method of claim 1 further comprising analyzing said collected substrate and altered substrate by laser induced fluorescence.

15. The method of claim 1 further comprising utilizing said collected substrate.

16. The method of claim 1 wherein said collecting comprises collecting with a microlumen of a capillary of a micropipette.

17. The method of claim 1 wherein said collecting comprises collecting with a microlumen of a microfabricated channel.

18. The method of claim 1 wherein said collecting comprises collecting with a microlumen, and further comprises aspirating into said microlumen.

19. The method of claim 18 wherein said aspirating comprises aspirating into a capillary of a micropipette.

20. The method of claim 18 wherein said aspirating into said microlumen comprises aspirating into a microfabricated channel.

21. The method of claim 1 wherein said collecting comprises collecting with a microlumen, and comprises collecting within one second of producing the laser generated shock wave.

22. The method of claim 1 wherein said collecting comprises collecting with a microlumen within 33 msec of producing the laser generated shock wave.

23. The method of claim 1 wherein said collecting comprises collecting with a microlumen within 10 microseconds of producing the laser generated shock wave.

24. The method of claim 1 wherein said collecting comprises collecting with a microlumen within 1 microsecond of producing the laser generated shock.

25. The method of claim 1 further comprising analyzing said substrate after lysis by an analysis device, wherein said substrate has no substantial difference in form between the condition of said substrate before and after lysing.

* * * * *

UNITED STATES PATENT AND TRADEMARK OFFICE
CERTIFICATE OF CORRECTION

PATENT NO. : 7,157,223 B2
APPLICATION NO. : 09/945396
DATED : January 2, 2007
INVENTOR(S) : Nancy Allbritton et al.

It is certified that error appears in the above-identified patent and that said Letters Patent is hereby corrected as shown below:

On the title page item (56)
In Other Publications:

Page 2, col. 1, line 5, please delete "XP002239303" and insert --XP02290903--.
Page 2, col. 1, line 33, please delete "Biol.I" and insert --Biol.--.
Page 2, col. 1, line 45, please delete "Separation" and insert --Separations--.
Page 2, col. 2, line 35, please delete "24240" and insert --2420--.

Signed and Sealed this

Thirteenth Day of November, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial
<220> FEATURE:
```

-continued

```
<223> OTHER INFORMATION: based on phosphorylation site of delta-CREB
      (Colbran et al.,Biochem. Cell Bio. 70:1277-82 (1992))

<400> SEQUENCE: 1

Lys Arg Arg Glu Ile Leu Ser Arg Arg Pro Ser Tyr Arg
1               5                   10

<210> SEQ ID NO 2
<211> LENGTH: 12
<212> TYPE: PRT
<213> ORGANISM: artificial
<220> FEATURE:
<223> OTHER INFORMATION: consensus phosphorylation site and reporter for
      cdc2 kinase. (Srinivasan et al, Biochemical J. 309:927-31 (1995)).

<400> SEQUENCE: 2

Gly Gly Gly Arg Ser Pro Gly Arg Arg Arg Arg Lys
1               5                   10
```